US010817965B2

(12) United States Patent
Rock

(10) Patent No.: US 10,817,965 B2
(45) Date of Patent: Oct. 27, 2020

(54) DYNAMIC VIDEO SCRIPTING SYSTEM AND METHOD

(71) Applicant: Eric Rock, Plano, TX (US)

(72) Inventor: Eric Rock, Plano, TX (US)

(73) Assignee: VIVIFY HEALTH, INC., Plano, TX (US)

( * ) Notice: Subject to any disclaimer, the term of this patent is extended or adjusted under 35 U.S.C. 154(b) by 1126 days.

(21) Appl. No.: 14/223,815

(22) Filed: Mar. 24, 2014

(65) Prior Publication Data

US 2014/0298173 A1    Oct. 2, 2014

Related U.S. Application Data

(63) Continuation-in-part of application No. 14/223,652, filed on Mar. 24, 2014, now Pat. No. 9,357,238, and a continuation-in-part of application No. 14/223,537, filed on Mar. 24, 2014, now Pat. No. 9,619,849.

(60) Provisional application No. 61/805,355, filed on Mar. 26, 2013.

(51) Int. Cl.
*G06Q 50/22*    (2018.01)
*G16H 40/63*    (2018.01)

(52) U.S. Cl.
CPC .............. *G06Q 50/22* (2013.01); *G16H 40/63* (2018.01)

(58) Field of Classification Search
CPC ........ G06Q 50/22; G06Q 50/24; G06Q 40/08; G06Q 10/10; G06F 19/322
See application file for complete search history.

(56) References Cited

U.S. PATENT DOCUMENTS

| 5,940,801 A | * | 8/1999 | Brown ................ G06F 19/322 273/429 |
| 7,593,952 B2 | | 9/2009 | Soll et al. |
| 7,739,126 B1 | | 6/2010 | Cave et al. |

(Continued)

FOREIGN PATENT DOCUMENTS

WO    WO 2013033655 A1    3/2013

OTHER PUBLICATIONS

Doukas, et. al., "Mobile Healthcare Information management Utilizing Cloud Computing and Android OS"; 32nd Annual International Conference of the IEEE EMBS Buenos Aires, Argentina, Aug. 31-Sep. 4, 2010.

*Primary Examiner* — Michael Tomaszewski
(74) *Attorney, Agent, or Firm* — David W. Carstens; Carstens & Cahoon, LLP

(57) ABSTRACT

A system and method dynamically presenting video content based on a visually-defined scripting editor that defines a user presentation context (UPC) based on audio/video content, user query/responses, and one or more asynchronous event triggers (AETs) is disclosed. The system incorporates a graphical user interface (GUI) based scripting editor operating on a host computer system (HCS) that enables visual definition of an interconnected video script network (VSN) that may include synchronously displayed content, decision-based content, and/or content dictated by the AETs. The VSN is converted to a video script dataset (VSD) by the HCS and then transmitted over a computer communication network (CCN) to a mobile user device (MUD) that executes the VSD in a user interface context (UIC) that may include the MUD, other devices such as a video display unit (VDU), and/or external data sourcing devices that may constitute the sources for the AETs.

27 Claims, 16 Drawing Sheets

(56) References Cited

U.S. PATENT DOCUMENTS

| | | |
|---|---|---|
| 8,183,998 B2 | 5/2012 | Rao et al. |
| 8,239,903 B1 | 8/2012 | Campagna et al. |
| 8,301,233 B2 | 10/2012 | Zhang et al. |
| 8,321,808 B2 | 11/2012 | Goetz et al. |
| 8,326,651 B2 | 12/2012 | McLaren et al. |
| 8,396,804 B1 | 3/2013 | Dala et al. |
| 2002/0184055 A1 | 12/2002 | Naghavi et al. |
| 2003/0022141 A1 | 1/2003 | Packard |
| 2003/0176790 A1 | 9/2003 | Slayton et al. |
| 2004/0039254 A1* | 2/2004 | Stivoric ............... A61B 5/0205 600/300 |
| 2004/0102931 A1 | 5/2004 | Ellis et al. |
| 2005/0102160 A1 | 5/2005 | Brown |
| 2005/0283385 A1 | 12/2005 | Hunkeler et al. |
| 2006/0030890 A1 | 2/2006 | Cosentino et al. |
| 2006/0122469 A1 | 6/2006 | Martel |
| 2006/0234202 A1 | 10/2006 | Brown |
| 2007/0006322 A1 | 1/2007 | Karimzadeh et al. |
| 2007/0015974 A1 | 1/2007 | Higgins et al. |
| 2007/0116036 A1 | 5/2007 | Moore |
| 2007/0191070 A1 | 8/2007 | Rao |
| 2007/0198653 A1 | 8/2007 | Jarnagin et al. |
| 2007/0255345 A1 | 11/2007 | Krause |
| 2008/0077436 A1 | 3/2008 | Muradia |
| 2008/0242947 A1 | 10/2008 | Jung et al. |
| 2008/0275317 A1 | 11/2008 | Cho et al. |
| 2008/0281633 A1 | 11/2008 | Burdea et al. |
| 2009/0012818 A1 | 1/2009 | Rodgers |
| 2009/0150416 A1 | 6/2009 | Baker et al. |
| 2011/0029327 A1 | 2/2011 | Dunlop |
| 2011/0166884 A1 | 7/2011 | Lesselroth et al. |
| 2011/0234409 A1 | 9/2011 | Soliman |
| 2011/0238435 A1 | 9/2011 | Rapaport et al. |
| 2011/0295621 A1 | 12/2011 | Farooq et al. |
| 2012/0041771 A1 | 2/2012 | Cosentino et al. |
| 2012/0041783 A1 | 2/2012 | McKee et al. |
| 2012/0183941 A1 | 7/2012 | Steinmetz |
| 2012/0203573 A1 | 8/2012 | Mayer et al. |
| 2012/0330684 A1 | 12/2012 | Jacobs et al. |
| 2013/0035955 A1 | 2/2013 | Torres |
| 2013/0117044 A1 | 5/2013 | Kalamas |
| 2013/0138450 A1 | 5/2013 | Vigneux |
| 2013/0238360 A1 | 9/2013 | Bhathal |
| 2013/0262155 A1 | 10/2013 | Hinkamp |
| 2013/0329058 A1 | 12/2013 | Brossette et al. |
| 2013/0339060 A1 | 12/2013 | Delaney et al. |
| 2016/0006946 A1 | 1/2016 | Cohen et al. |

* cited by examiner

DYNAMIC VIDEO SCRIPTING SYSTEM AND METHOD

CROSS REFERENCE TO RELATED APPLICATIONS

U.S. Provisional Patent Applications

This application claims benefit under 35 U.S.C. § 119 and incorporates by reference United States Provisional patent application for HEALTHCARE MANAGEMENT SYSTEM AND METHOD by inventor Eric Rock, filed electronically with the USPTO on Mar. 26, 2013, with Ser. No. 61/805,355, EFS ID 15358332, confirmation number 6386.

U.S. Utility Patent Applications

This application claims benefit under 35 U.S.C. § 120 and incorporates by reference United States Utility patent application for HEALTHCARE DELIVERY SYSTEM AND METHOD by inventor Eric Rock, filed electronically with the USPTO on Mar. 24, 2014, with Ser. No. 14/223,537, EFS ID 18566745, confirmation number 2107. This patent application will be referred to herein as the HEALTHCARE DELIVERY SYSTEM AND METHOD patent application.

This application claims benefit under 35 U.S.C. § 120 and incorporates by reference United States Utility patent application for VIDEO DATA EXTENSION SYSTEM AND METHOD by inventor Eric Rock, filed electronically with the USPTO on Mar. 24, 2014, with Ser. No. 14/223,652, EFS ID 18567689, confirmation number 1380. This patent application will be referred to herein as the VIDEO DATA EXTENSION SYSTEM AND METHOD patent application.

U.S. Continuation-In-Part (CIP) Patent Application

This application is a continuation-in-part (CIP) patent application of and incorporates by reference United States Utility patent application for HEALTHCARE DELIVERY SYSTEM AND METHOD by inventor Eric Rock, filed electronically with the USPTO on Mar. 24, 2014, with Ser. No. 14/223,537, EFS ID 18566745, confirmation number 2107. This patent application will be referred to herein as the HEALTHCARE DELIVERY SYSTEM AND METHOD patent application.

This application is a continuation-in-part (CIP) patent application of and incorporates by reference United States Utility patent application for VIDEO DATA EXTENSION SYSTEM AND METHOD by inventor Eric Rock, filed electronically with the USPTO on Mar. 24, 2014, with Ser. No. 14/223,652, EFS ID 18567689, confirmation number 1380. This patent application will be referred to herein as the VIDEO DATA EXTENSION SYSTEM AND METHOD patent application.

PARTIAL WAIVER OF COPYRIGHT

All of the material in this patent application is subject to copyright protection under the copyright laws of the United States and of other countries. As of the first effective filing date of the present application, this material is protected as unpublished material.

However, permission to copy this material is hereby granted to the extent that the copyright owner has no objection to the facsimile reproduction by anyone of the patent documentation or patent disclosure, as it appears in the United States Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO A MICROFICHE APPENDIX

Not Applicable

FIELD OF THE INVENTION

The present invention generally relates to systems and methods for integrating multimedia audio/video sources for presentation to a user on mobile and non-mobile devices. Without limiting the scope of the present invention, the present invention may be advantageously applied to healthcare delivery systems that incorporate mobile deployment of scripted video content that is responsive to healthcare provider directives, patient interaction, and input from medical instrumentation devices configured for patient monitoring.

PRIOR ART AND BACKGROUND OF THE INVENTION

Prior Art System Context

Within the context of automated healthcare delivery systems there is often a need for multimedia audio/video content to be displayed on a mobile user device (MUD) such as computer tablets, smartphones, laptops, and the like. This content often involves diverse sources of information including modal dialogs, status information displays, audio content, video content, and the like. Within this context there are often situations in which the content presented to a patient must be presented with a variety of different multimedia options that are defined based on a wide variety of factors. These factors may include actions that are responsive to the collection of medical data from the patient, directives from healthcare professionals, and other information. Furthermore, these factors may need to be dictated by an overarching patient healthcare plan (PHP) that defines the healthcare delivery to be proffered to the patient.

Closely aligned with this application context are issues relating to the presentation of multimedia content to a patient in situations where asynchronous data triggers a video or other multimedia content and an associated scripted interaction with a patient. The prior art has detailed techniques in which healthcare related content may be synchronously presented to a patient, but the issue of asynchronous event triggers has not been addressed by the prior art. Furthermore, the tools used in these contexts have typically been targeted towards skilled computer programmers. As such, traditional healthcare personnel are not able to easily modify these patient displays without skilled help from a technical professional. This results in severe difficulty in updating educational materials for patients who have dynamically changing medical conditions.

However, currently there is no methodology seamlessly integrate audio/video content together in this context to permit its proper presentation to the patient under these conditions. While web-based static displays and modal dialogs are currently used to provide patient information in many healthcare settings, the ability to integrate video scripting in this context and properly integrate this with a patient healthcare plan (PHP) has not been solved by the prior art.

Deficiencies in the Prior Art

The prior art as detailed above suffers from the following deficiencies:
Prior art video scripting systems and methods do not permit integration of video content with static web displays.
Prior art dynamic video scripting systems and methods do not permit both synchronous and asynchronous processing of video content.
Prior art dynamic video scripting systems and methods do not permit video content to be displayed based on information retrieved from medical instrumentation devices (MIDs).
Prior art dynamic video scripting systems and methods do not permit unskilled individuals the opportunity to script video in a heuristic manner.
Prior art dynamic video scripting systems and methods do not permit coordination of scripted video with a patient healthcare plan (PHP).
Prior art dynamic video scripting systems and methods do not permit autonomous operation on remote mobile user devices (MUDs) without host communication.

While some of the prior art may teach some solutions to several of these problems, the core issue of scripting a video experience for the user in a healthcare context has not been solved by the prior art.

OBJECTIVES OF THE INVENTION

Accordingly, the objectives of the present invention are (among others) to circumvent the deficiencies in the prior art and affect the following objectives in the context of a dynamic video scripting system and method:
(1) Provide for a dynamic video scripting system and method that permits integration of video content with static web displays.
(2) Provide for a dynamic video scripting system and method that permits both synchronous and asynchronous processing of video content.
(3) Provide for a dynamic video scripting system and method that permits video content to be displayed based on information retrieved from medical instrumentation devices (MIDs).
(4) Provide for a dynamic video scripting system and method that permits unskilled individuals the opportunity to script video in a heuristic manner.
(5) Provide for a dynamic video scripting system and method that permits coordination of scripted video with a patient healthcare plan (PHP).
(6) Provide for a dynamic video scripting system and method that permits autonomous operation on remote mobile user devices (MUDs) without host communication.

While these objectives should not be understood to limit the teachings of the present invention, in general these objectives are achieved in part or in whole by the disclosed invention that is discussed in the following sections. One skilled in the art will no doubt be able to select aspects of the present invention as disclosed to affect any combination of the objectives described above.

BRIEF SUMMARY OF THE INVENTION

The present invention system and method permit a scripting video editor to integrate modal/event-driven control structures to allow presentation of multimedia audio/video to a user based on synchronized scripting information but also in response to user inputs and asynchronous events that may be identified within the scripting language. The video stream may incorporate dynamic user input "tags" that may trigger asynchronous event processing tasks by either a host computer system (HCS) or remote mobile user device (MUD) processors. The system/method anticipates tight integration to patient monitoring such that the remote mobile user device (MUD) can be configured with "self-help" videos that are triggered based on patient history in conjunction with other data taken from patient monitoring instruments. This permits a "look and feel" to mimic a patient care professional rather than traditional modal dialog user interfaces. The system described herein may be combined with a dynamic video scripting method used to affect integration of a variety of video sources for simultaneous albeit disparate display on a number of different video hardware displays.

BRIEF DESCRIPTION OF THE DRAWINGS

For a fuller understanding of the advantages provided by the invention, reference should be made to the following detailed description together with the accompanying drawings wherein.

DESCRIPTION OF THE PRESENTLY PREFERRED EXEMPLARY EMBODIMENTS

Figure 1:
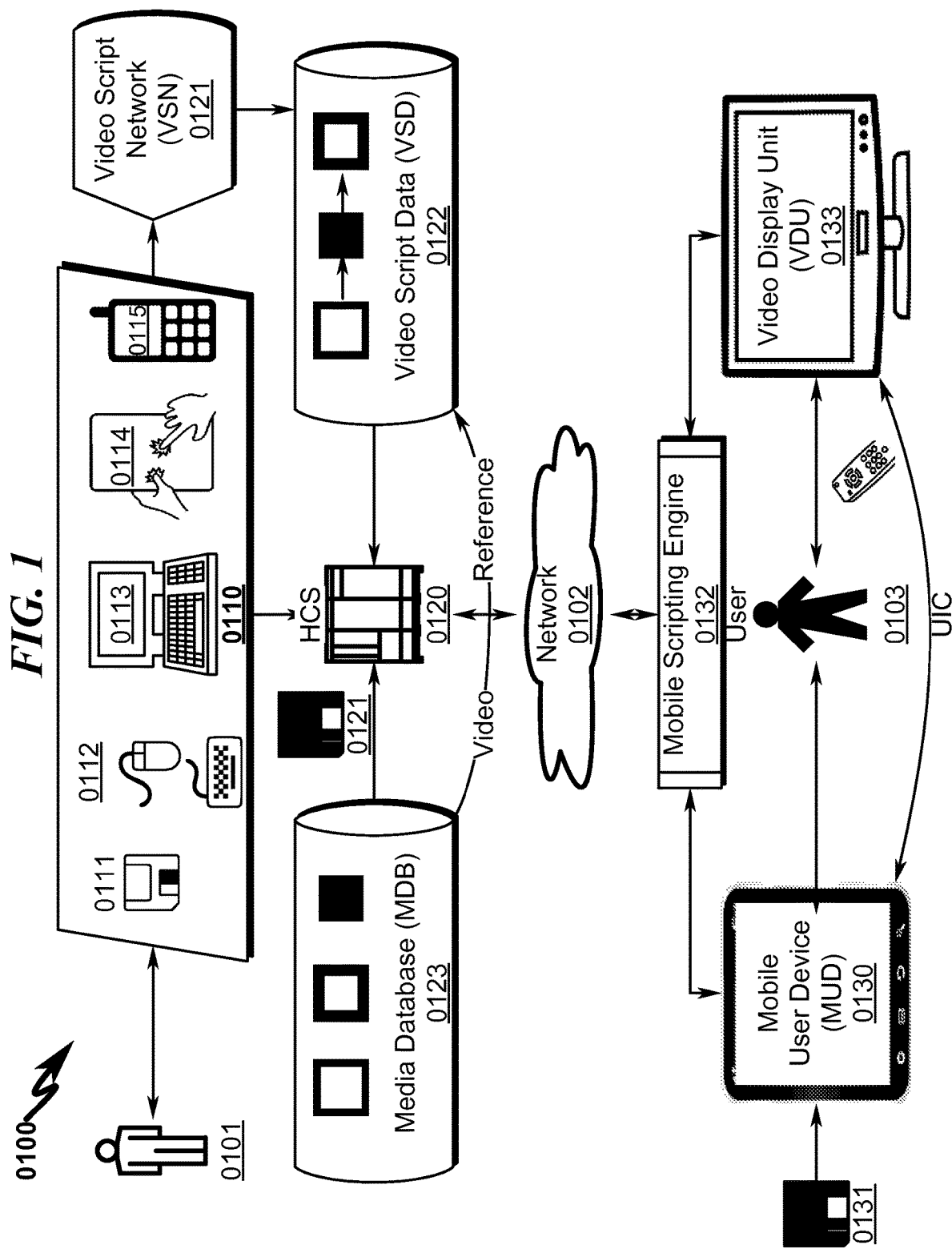
FIG. 1 illustrates an exemplary dynamic video scripting system context.

While this invention is susceptible of embodiment in many different forms, there is shown in the drawings and will herein be described in detailed preferred embodiment of the invention with the understanding that the present disclosure is to be considered as an exemplification of the principles of the invention and is not intended to limit the broad aspect of the invention to the embodiment illustrated.

The numerous innovative teachings of the present application will be described with particular reference to the presently preferred embodiment, wherein these innovative teachings are advantageously applied to the particular problems of a DYNAMIC VIDEO SCRIPTING SYSTEM AND METHOD. However, it should be understood that this embodiment is only one example of the many advantageous uses of the innovative teachings herein. In general, statements made in the specification of the present application do not necessarily limit any of the various claimed inventions. Moreover, some statements may apply to some inventive features but not to others.

Video Content Display not Limitive

Within the description of the present invention provided herein the audio and/or video content described herein may be configured to span multiple displays such as described in the VIDEO DATA EXTENSION SYSTEM AND METHOD patent application that is incorporated by reference herein. Thus, the video scripting concepts described herein may incorporate user interaction context (UIC) commands that dictate the presentation of and input from a variety of video displays such as that provided by the mobile user device (MUD) and/or a video display unit (VDU).

System Overview (0100)

The present invention may be summarized as depicted in the system block diagram of FIG. 1 (0100), and is comprised of three cooperating computer systems as depicted by the operator interface computer (OIC) (0110), host computer system (HCS) (0120), and mobile user device (MUD) (0130). Each of these computer systems operates under control of machine instructions read from computer readable medium (0111, 0121, 0131). Within this context the system operates to generate a video script network (VSN) (0121) that is defined using the OIC (0110) via a variety of input devices (0112, 0113, 0114, 0115) under control of an video scripting operator (0101). This VSN (0121) is converted into a video script dataset (0122) that references data retrieved from a media database (MDB) (also termed a video database (VDB) (0123) the VSN (0121) describes the sequencing of display information retrieved from the (MDB) (0123) and the interaction of this content with a remote user (0103).

The VSD (0122) is communicated by the HCS (0120) to a mobile user device (0130) over a computer communication network (0102) (typically the Internet). The MUD executes a mobile scripting engine (MSE) (0132) that interprets the VSD (0122) and retrieves content from the MDB (0123) for presentation to a user (0103) on the MUD (0130) and/or a video display unit (VDU) (0133). The MSE (0132) operating in the context of the MUD (0130) may incorporate a variety of user interaction contexts (UIC) that define the integration of the deployed multimedia content among the various I/O devices (MUD (0130) and VDU (0133).

Method Overview (0200)

Figure 2:
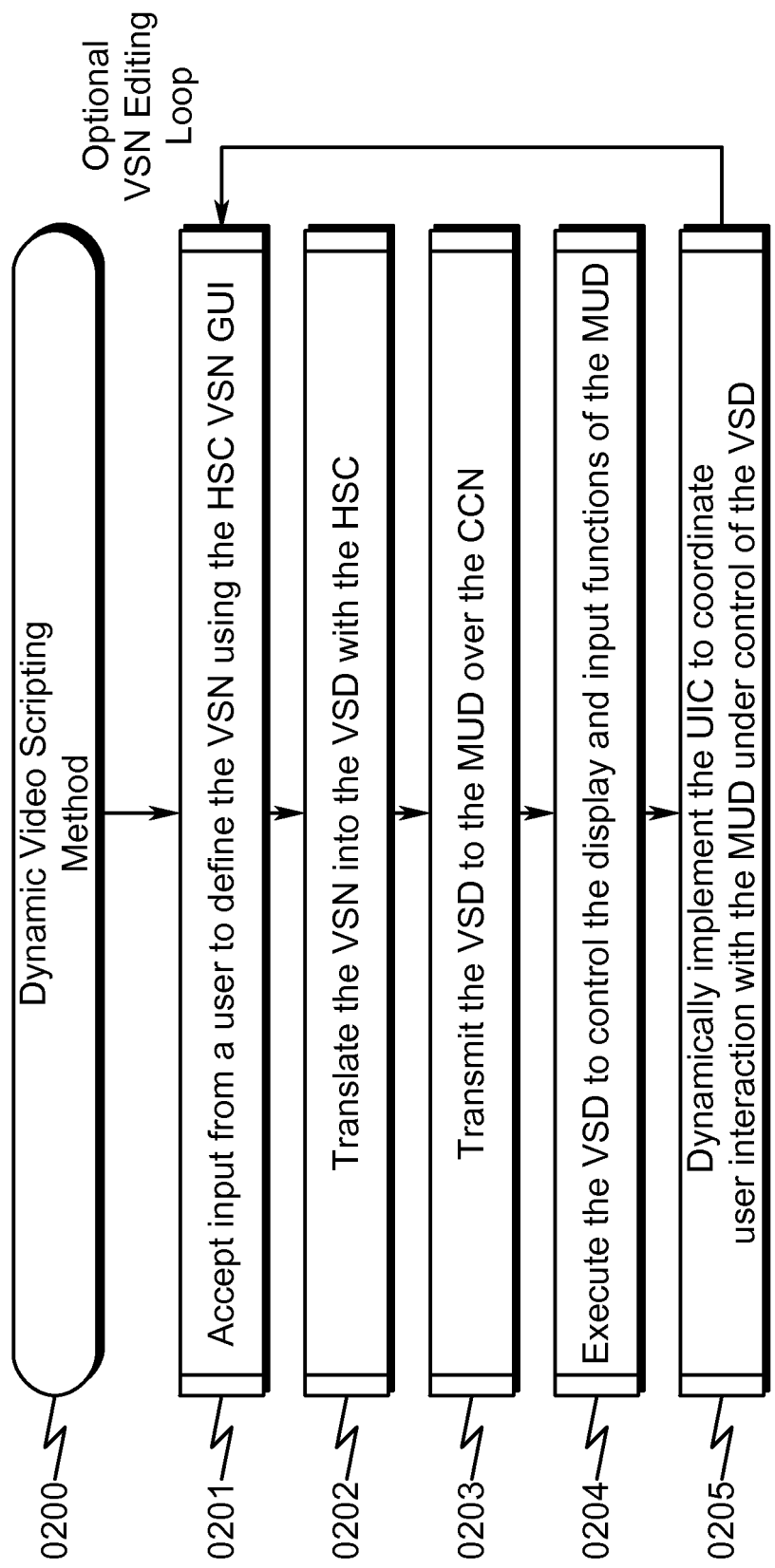
FIG. 2 illustrates an exemplary dynamic video scripting method.

The system context as depicted in FIG. 1 (0100) is typically associated with a methodology as depicted in FIG. 2 (0200) and involves the following steps:
(1) with the HCS, accepting input from a user to define the VSN using the GUI (0201);
(2) with the HCS, translating the VSN into the VSD (0202);
(3) with the HCS, transmitting the VSD to the MUD over the CCN (0203);
(4) with the MUD, executing the VSD to control the display and input functions of the MUD (0204); and
(5) with the MUD, dynamically implementing the UIC to coordinate user interaction with the MUD under control of the VSD (0205).

Note that both the UIC execution by the VCU and the potential UIC selection by the MUD may occur in real-time.

System Embodiment Detail (0300)

Figure 3:
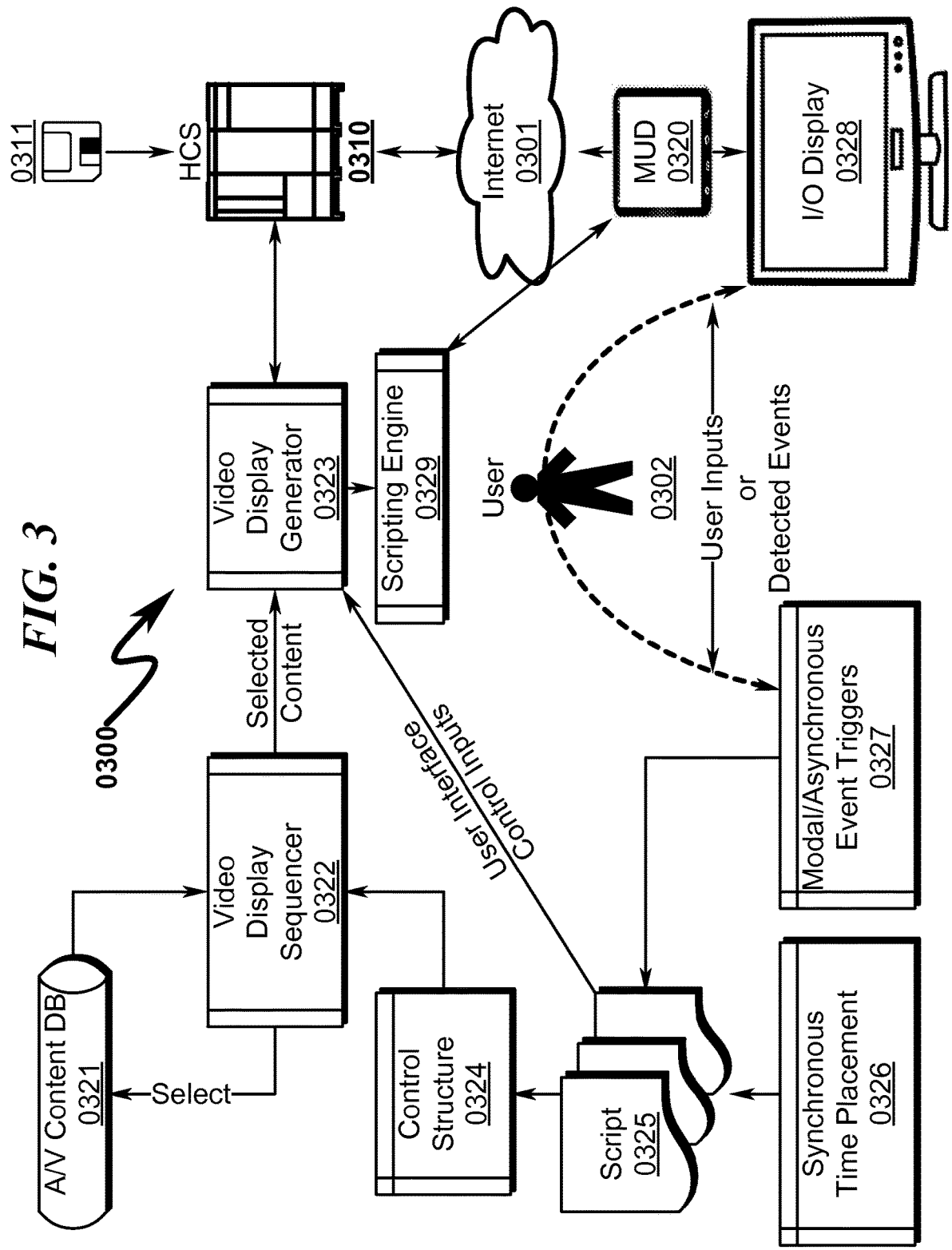
FIG. 3 illustrates a preferred exemplary overview block diagram of a preferred exemplary system embodiment of the present invention.

Additional detail of a preferred system embodiment is depicted in the system block diagram of FIG. 3 (0300), wherein the HCS (0310) communicates with the MUD (0320) over the Internet (0301) to deploy video content (0321) that has been sequenced (0322) via a video script network to select video content (0323) that is displayed according to a control structure (0324) defined by the video script (0325). This video script (0325) may incorporate synchronous time placement (0326) of video content as well as modal/asynchronous event triggers (AET) (0327) based video content. The AET (0327) controls may be provided by user inputs and/or detected events in the user (0302) environment. The MUD (0320) may be configured to display this scripted video content locally or in conjunction with a video display unit (VDU) (0328). The MUD scripting engine (0329) coordinates display of the scripted video content on the MUD (0320) and/or the auxiliary video display (0328).

Healthcare System Embodiment Overview (0400)

Figure 4:
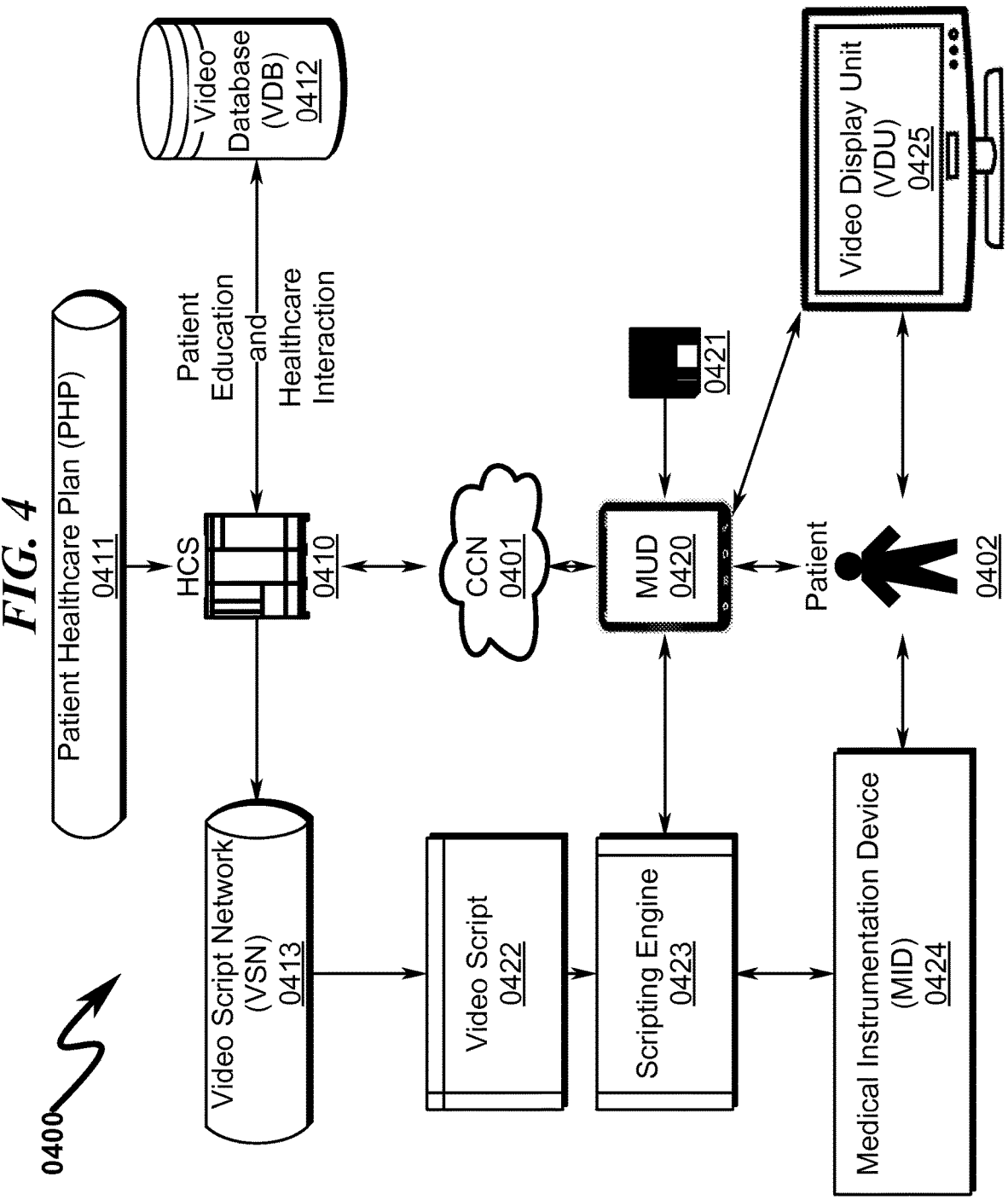
FIG. 4 illustrates a preferred exemplary overview flowchart of a preferred exemplary method embodiment of the present invention.

The present invention as applied to a healthcare system application context may be summarized as depicted in the system block diagram of FIG. 4 (0400). In this example a host computer system (HCS) (0410) that may incorporate a healthcare web server (HWS) is used to define a patient healthcare plan (PHP) (0411) that is used to coordinate the healthcare delivery through a computer network (0401) to a patient (0402). The HCS (0410) when creating the PHP (0411) may have need of the presentation of education materials and other visual information to the patient (0402) that is created and stored in a video database (VDB) (0412). This visual information may need to be presented to the patient (0402) in a coordinated fashion based on a complex set of criterion that precludes the generation of a single video sequence for presentation to the patient (0402).

To solve this HCS (0410) and PHP (0411) interaction problem with the patient (0402), a video script network (VSN) (0413) is created on the HCS (0410) that describes a controlled video flow to be presented to the patient (0402) based on a variety of conditions local to the patient (0402). This VSN (0413) is converted into a video script dataset (VSD) (0422) that is interpreted by a scripting engine (0423) for presentation on the MUD (0410) using both synchronous presentation methodologies but also asynchronous presentation methodologies that may make sue of asynchronous event triggers (AETs) derived from input from medical instrumentation devices (MIDs) configured to monitor the healthcare parameters of the patient (0402). Within this context the scripting engine (0423) may also permit integration of I/O devices such as a video display unit (VDU) (0425) in conjunction with the MUD (0420) display.

A core concept in this architecture is that the PHP (0411) is configurable by healthcare providers from the hospital or other medical facility care management team members to continually drive real-time healthcare to the patient (0402) through the MUD (0410). This may include educational materials, real-time interaction with healthcare providers, as well as dynamic display of video based on measured patient medical parameters.

Healthcare Method Integration

Associated with the exemplary system overview described in FIG. 4 (0500) is a dynamic video scripting method applied to a healthcare delivery method that comprises the following steps:
(1) Collecting patient data in real-time within a HIS/EMR infrastructure;
(2) Allowing definition of a patient healthcare plan (PHP) that coordinates delivery of healthcare to a patient;
(3) Integrating remote patient monitoring (RPM) data from mobile patient monitoring devices and patient alerts based on execution of the PHP;
(4) Risk stratifying all active patients to queue prioritized healthcare delivery to patients;
(5) Displaying risk stratification dashboards in real-time to trigger healthcare provider activity on specific patients;
(6) Updating/clearing alert status once patient status is improved/modified;
(7) Allowing the PHP be updated to adjust patient healthcare strategy based on patient alerts; and
(8) Triggering patient questionnaires/video scripts and/or external interaction on the MUD between the patient and healthcare professionals using a dynamic video script based on alerts generated by and user interaction contexts defined by the PHP and then proceeding to step (1).

One skilled in the art will recognize that these method steps may be augmented or rearranged without limiting the teachings of the present invention. This general method summary may be augmented by the various elements described herein to produce a wide variety of invention embodiments consistent with this overall design description.

Note that in step (8) the process may rely heavily on the integration of the MUD and VDU displays in order to coordinate the deployment of the PHP to the patient in a directed or autonomous fashion. For example, the PHP may dictate a conference call with a healthcare provider that has access to the patient medical information as well as instructional videos that should be provided to the patient to improve their overall healthcare. This information may be deployed to the MUD and/or VCU for presentation to the patient in a coordinated multi-display multi-media fashion as defined by a user interaction context (UIC) described herein. This UIC may be dictated by the PHP and/or MUD to provide for a patient user experience that surpasses that which would normally be available solely from the MUD display context. This UIC may be dictated by a video script on a dynamic basis in conjunction with direction from the patient healthcare plan (PHP).

Healthcare System Embodiment Overview (0500)

Figure 5:
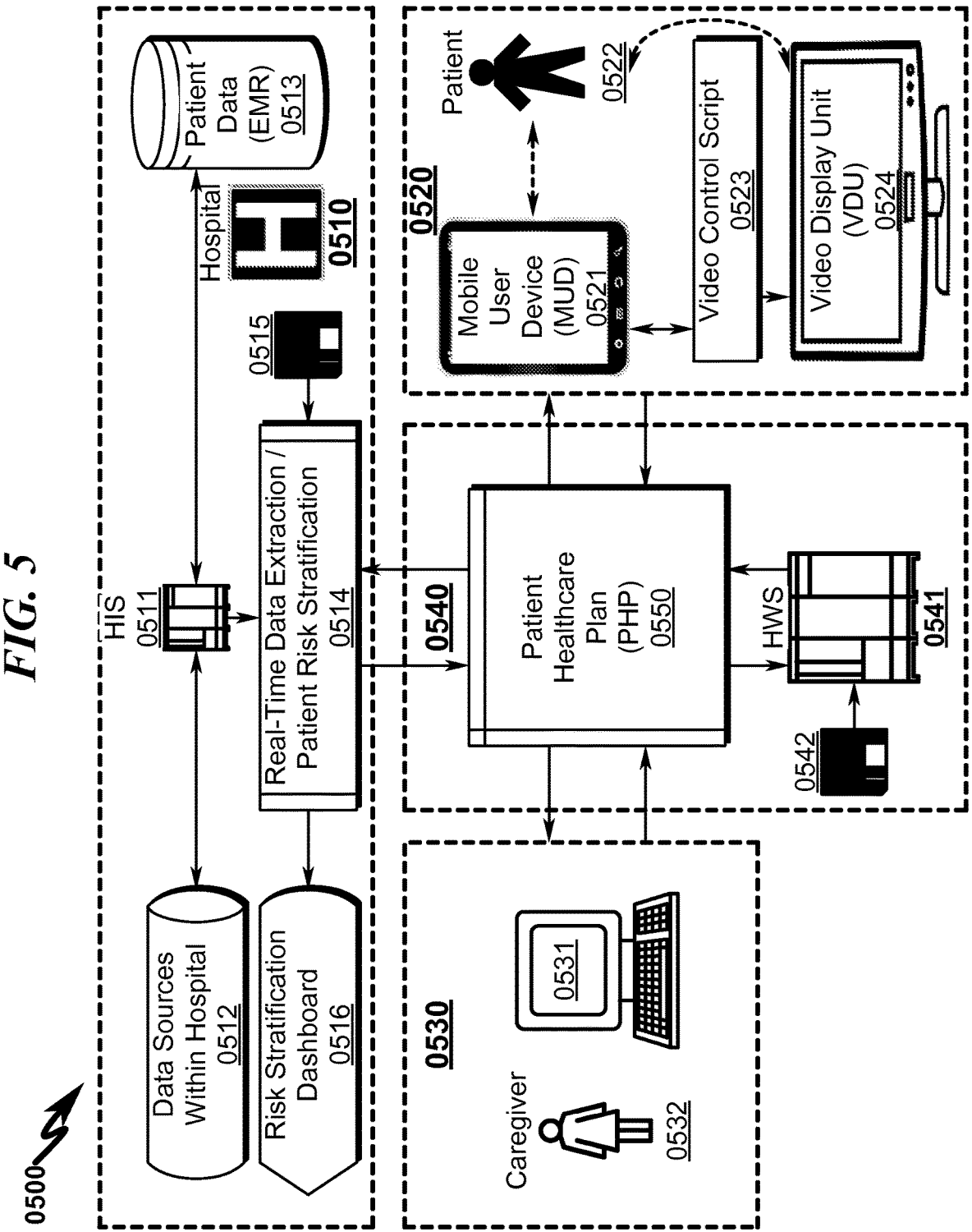
FIG. 5 illustrates a preferred exemplary data flow block diagram of a preferred exemplary system embodiment of the present invention as applied to patient healthcare delivery.

The present invention as applied to a healthcare system application context may be summarized as depicted in the system block diagram of FIG. 5 (0500), and is comprised of four cooperating computer systems as depicted by the HIS system (0510), patient remote monitoring system (0520), caregiver computer system(s) (0530), and healthcare web server (HWS) (0540) (also termed a host computer system (HCS) in this application). Within this context the system operates to integrate information from the various computer systems (0511, 0521, 0531, 0541) as dictated by an overarching patient healthcare plan (PHP) (0550) executed as machine instructions read from a computer readable medium (0542) that drives information flow between the various computer systems (0511, 0521, 0531, 0541).

A core concept in this architecture is that the PHP (0550) is configurable by healthcare providers from the hospital (0510) or other medical facility care management team members to continually drive real-time healthcare dashboard status information to authorized healthcare provider recipients based on real-time patient information collected from remote monitoring devices (RMD) communicating with mobile user devices (MUD) (0521) as well as information gathered from patient caregiver interfaces (0531) and information collected from real-time data extraction processes (0514) operating within the HIS (0511) environment. Since current healthcare methodologies isolate the HIS (0511) system within the context of a defined hospital (0510) healthcare environment, coordination of information among healthcare professionals after the patient leaves this environment has been problematic. By providing a healthcare web server (HWS) (0540) incorporating web portals accessible by the authorized healthcare providers, the system as depicted permits a unified patient healthcare plan (PHP) (0550) to act as the driver for the delivery of healthcare to the patient as well as the hub for reporting patient status to all interested and authorized healthcare professionals servicing the patient.

Within the context of the hospital setting (0510), data is continually collected by the healthcare information system (HIS) (0511) computer from a wide variety of data sources (0512) such as lab results, patient history information, chart diagnoses, procedures, surgeries, patient vital signs, etc. This information normally flows directly from the data sources (0512) to the HIS (0511) (via manual or automated input) and is collected for deposit within the patient electronic medical record (EMR) database (0513). The present invention inserts a software module (0514) (as executed machine instructions read from a computer readable medium (0515)) in this HIS (0511) context to sniff these data flows and extract information associated with various patients. This real-time patient data is then used as input to the patient healthcare plan (PHP) (0550) to drive patient care and also as input to a real-time process (0514) configured to risk stratify patients before and after they leave the hospital (0510) setting. This permits the care management team or other healthcare providers to have a real-time risk stratification dashboard (0516) that allows at-risk patients to be immediately identified for additional care or modifications to their PHP (0550). This is in contrast to prior art systems that are unable to gather patient data across various physician-care boundaries and integrate this information into a coherent risk stratification analysis.

By integrating in-patient information, out-patient information, and information gathered from various healthcare providers (0532), it is possible to immediately address declines in patient health with proactive measures rather than waiting until these conditions reach a critical stage necessitating readmission of the patient (0522) to the hospital (0510). Additionally, within the hospital (0510) context, the real-time integration of patient care information permits a real-time risk stratification dashboard (0516) to be created that allows hospital and care management staff the ability to allocate their limited resources to patients at the greatest risk of a severe medical event.

It is informative to note that less than 5% of the patient population account for 50% of the cost of patient care. Among this group, annual medical expenses equaled or exceeded USD$11487 per person. In contrast, the 50 percent of the population with the lowest healthcare expenses accounts for only about 3 percent of overall U.S. medical spending, with an annual medical spending below USD$664 per person. Thus, those in the top 5 percent of healthcare utilization spent on average more than 17 times as much per person as those in the bottom 50 percent of healthcare spenders. From this data it is clear that allocating resources optimally to at-risk patients can have a significant impact on the overall cost of healthcare within the hospital (0510) environment. The present invention in this context permits the hospital (0510) and other healthcare professionals (0532) the ability to maintain a real-time status dashboard of patient medical conditions and within this framework address at-risk patients immediately to minimize their overall cost to the healthcare delivery system.

With respect to the patient remote monitoring system (0520), the MUD (0521) operates as the main user (0522) interface, but with respect to the video scripting system embodiment described herein is augmented with a video scripting engine (0523) and video display unit (VDU) (0524) that are coordinated via the use of a user interface context (UIC) control that is executed within the script (0523) to coordinate mobile video content (MVC) provided by the overall healthcare system across the MUD (0521) and the VDU (0524). The patient healthcare plan (PHP) (0550) may be configured to dictate the operation of individual UIC modes that drive the coordinated MUD (0521) and VDU (0524) patient (0522) I/O experience.

It should be noted that in this healthcare delivery context the use of the VDU (0524) in conjunction with the MUD (0521) is significant in that many patients (0522) are elderly or visually impaired and the use of a MUD (0521) alone in this healthcare delivery application is therefore problematic. Integration of the MUD (0521) and the VDU (0524) provides for a more robust patient (0522) I/O experience that may overcome several of the disabilities associated with traditional patient care in this context.

Healthcare Method Embodiment Overview (0600)

Figure 6:
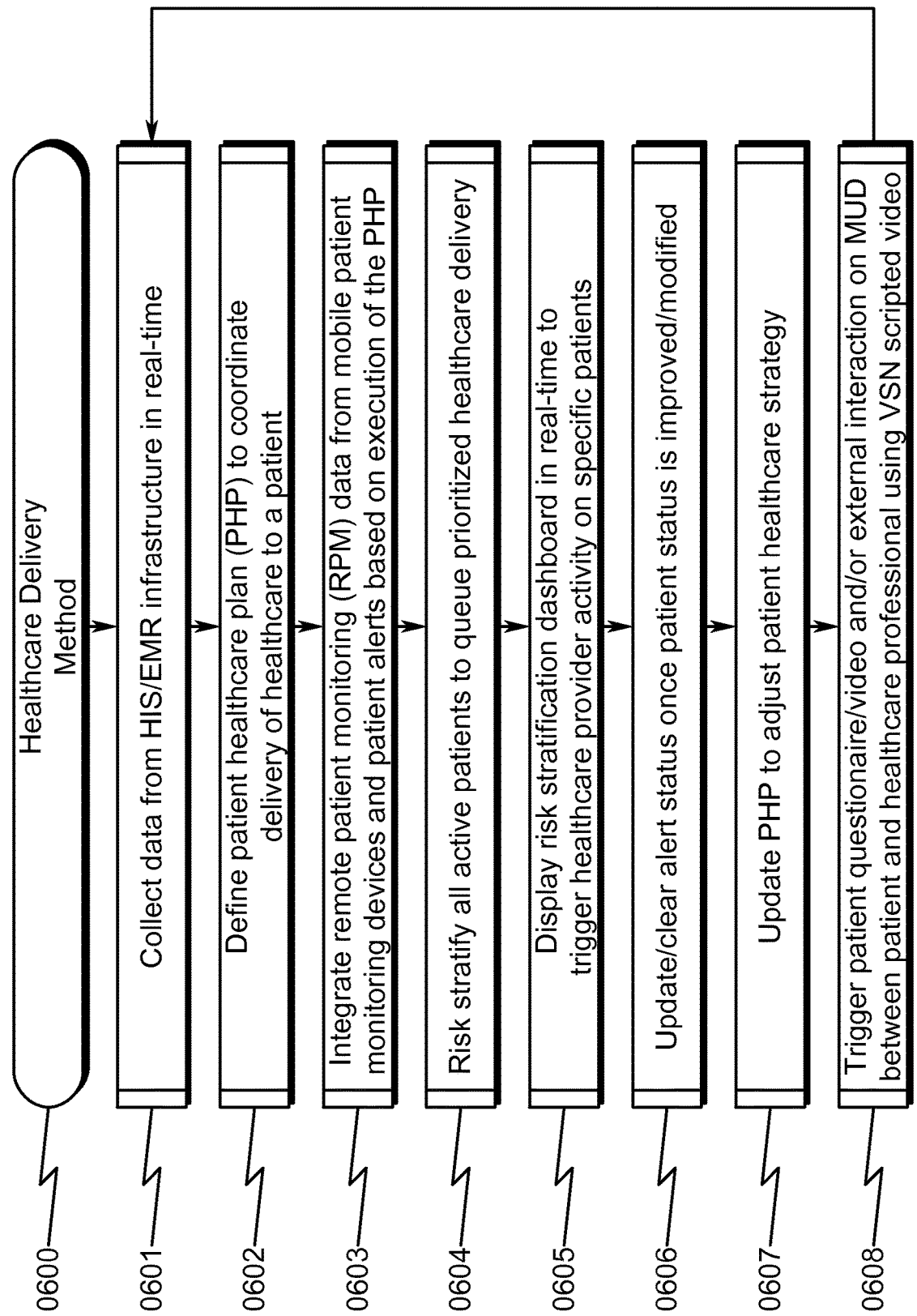
FIG. 6 illustrates a preferred exemplary flowchart of a preferred exemplary method embodiment of the present invention as applied to patient healthcare delivery.

Associated with the exemplary system overview described in FIG. 5 (0500) is a video data extension method applied to a healthcare delivery method as depicted in FIG. 6 (0600) that comprises the following steps:

(1) Collecting patient data in real-time within a HIS/EMR infrastructure (0601);
(2) Allowing definition of a patient healthcare plan (PHP) that coordinates delivery of healthcare to a patient (0602);
(3) Integrating remote patient monitoring (RPM) data from mobile patient monitoring devices and patient alerts based on execution of the PHP (0603);
(4) Risk stratifying all active patients to queue prioritized healthcare delivery to patients (0604);
(5) Displaying risk stratification dashboards in real-time to trigger healthcare provider activity on specific patients (0605);
(6) Updating/clearing alert status once patient status is improved/modified (0606);
(7) Allowing the PHP be updated to adjust patient healthcare strategy based on patient alerts (0607); and
(8) Triggering patient questionnaires/video and/or external interaction on the MUD between the patient and healthcare professionals using video script as defined by the VSN based on alerts generated by and user interaction contexts defined by the PHP and then proceeding to step (1) (0608).

One skilled in the art will recognize that these method steps may be augmented or rearranged without limiting the teachings of the present invention. This general method summary may be augmented by the various elements described herein to produce a wide variety of invention embodiments consistent with this overall design description.

Note that in step (8) the process may rely heavily on the integration of the MUD and VDU displays in order to coordinate the deployment of the PHP to the patient in a directed or autonomous fashion. For example, the PHP may dictate a conference call with a healthcare provider that has access to the patient medical information as well as instructional videos that should be provided to the patient to improve their overall healthcare. This information may be deployed to the MUD and/or VCU for presentation to the patient in a coordinated multi-display multi-media fashion as defined by a user interaction context (UIC) described herein. This UIC may be dictated by the PHP and/or MUD to provide for a patient user experience that surpasses that which would normally be available solely from the MUD display context.

Exemplary Video Script Editor GUI (0700)

Figure 7:
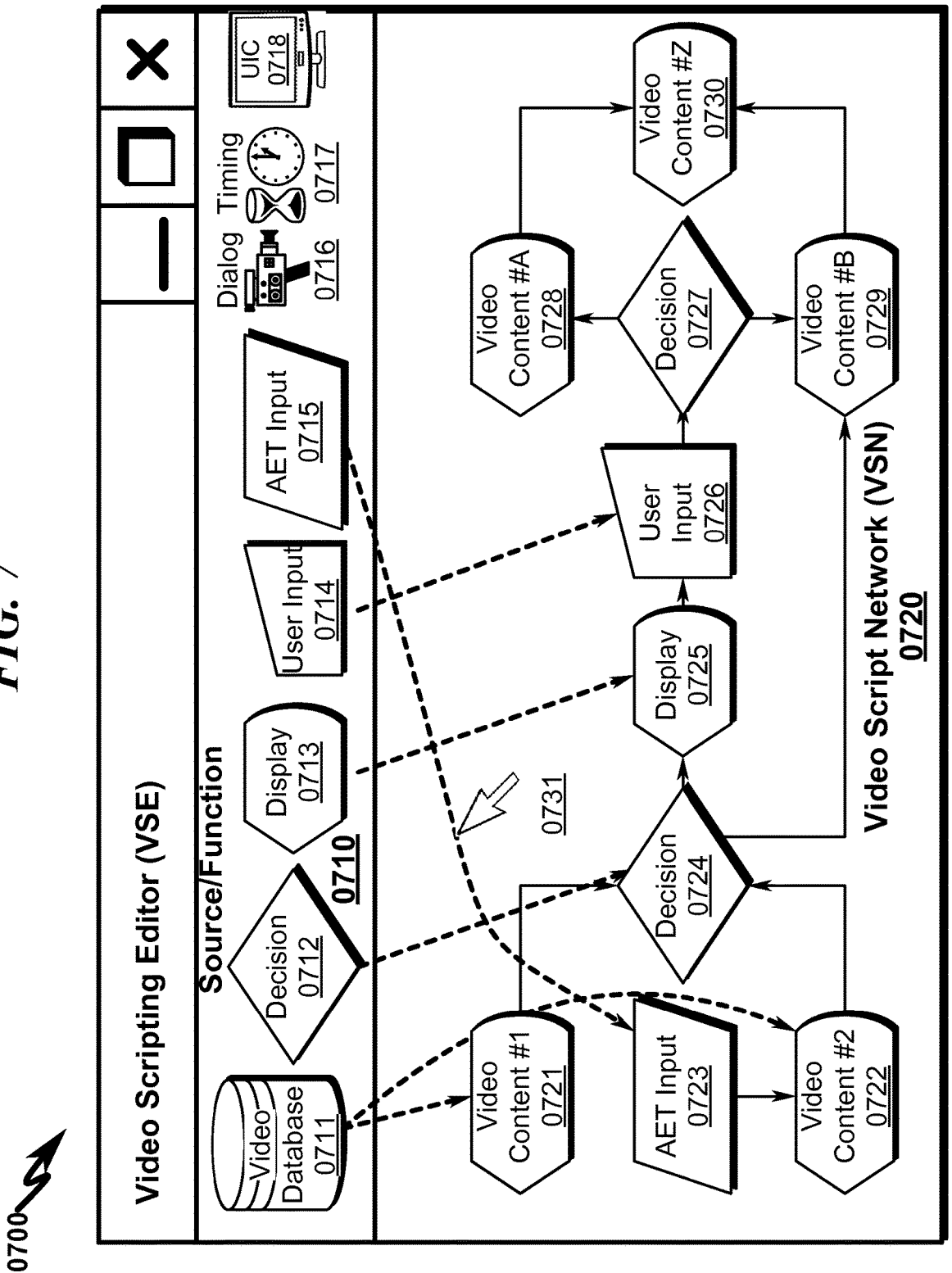
FIG. 7 illustrates an exemplary video scripting editor (VSE) graphical user interface (GUI) configured to permit the definition of a video script network (VSN) using source/function icons and connectors.

As depicted in FIG. 7 (0700), one presently preferred methodology of creating and editing video scripts incorporates a main graphical dialog toolbox (0710) that may comprise a variety of graphical video scripting icons (VSI) such as the following:

Video Database Sources (0711)—this icon permits insertion of multimedia audio/video content from a source database. In some circumstances this may include the capability to create on-the-fly video for insertion into the video stream or trigger a live video connection to support personnel within a pool of available consultants that are available on an on-demand video basis.

Decision Blocks (0712)—this icon permits insertion of a decision block that may have inputs associated with the result of previous events in the video stream such as the selection of a particular video, user input, or detected AET.

Modal/Static Display Blocks (0713)—this icon permits display of a static screen or modal display.

User Input Blocks (0714)—this icon permits entry of user data and may incorporate the necessary forms, radio button selections, and/or checkboxes to define a particular user data input key that is used for a decision block.

Asynchronous Event Trigger (AET) Blocks (0715)—this icon permits input from an asynchronous event, such as a timer, delay, medical instrumentation device, healthcare professional, PHP trigger, etc. These asynchronous events may trigger paths within the video script that may not occur during normal synchronous processing of the script.

Dialog Blocks (0716)—this icon permits triggering of interactive live video dialogs with a remote user selected from a source conference pool (SCP) of directed individuals.

Timed Display Blocks (0717)—this icon permits triggering of a script operation after absolute/relative delays or at a certain calendar time that may include repeated time activation based on a repeating calendar.

User Interaction Context (UIC) Blocks (0718)—this icon permits configuration of a UIC associated with the presentation of information on the MUD and/or an associated video display unit (VDU).

One skilled in the art will recognize that these elements are illustrative and not limitive of the present invention scope.

As depicted in the exemplary video script network (VSN) the scripting icons (0711, 0712, 0713, 0714, 0715, 0716, 0717, 0718) may be placed (via a mouse (0731) drag-and-drop methodology) and interconnected in a visual network that describes the operation of the video script. Synchronous and/or asynchronous paths within the video script may be supported. For example, the initial video display (0721) would be synchronously activated, but may be preempted by alternate video content (0722) based on input from an asynchronous event trigger (AET) (0723) input. The use of decision blocks (0724, 0727) within the video script may make a variety of paths active based on AET inputs (0723), user inputs (0726), or other activity such as delays and/or calendar timers (0717).

The present invention is configured to take this visual display and convert it to an internal video script dataset (VSD) that comprises a data structure mimicking the interconnection of this video script network. This VSD is conveyed to the MUD for autonomous execution to convey a particular user presentation context (UPC) that may comprise the presentation of the scripted video to a variety of displays (MUD, VDU, etc.) under control of a particular user interaction context (UIC) that may be defined within the VSE or by the PHP that may trigger activation of the VSN/VSD on the MUD.

Video Data Scripting Network Creation/Definition Method (0800)

Figure 8:
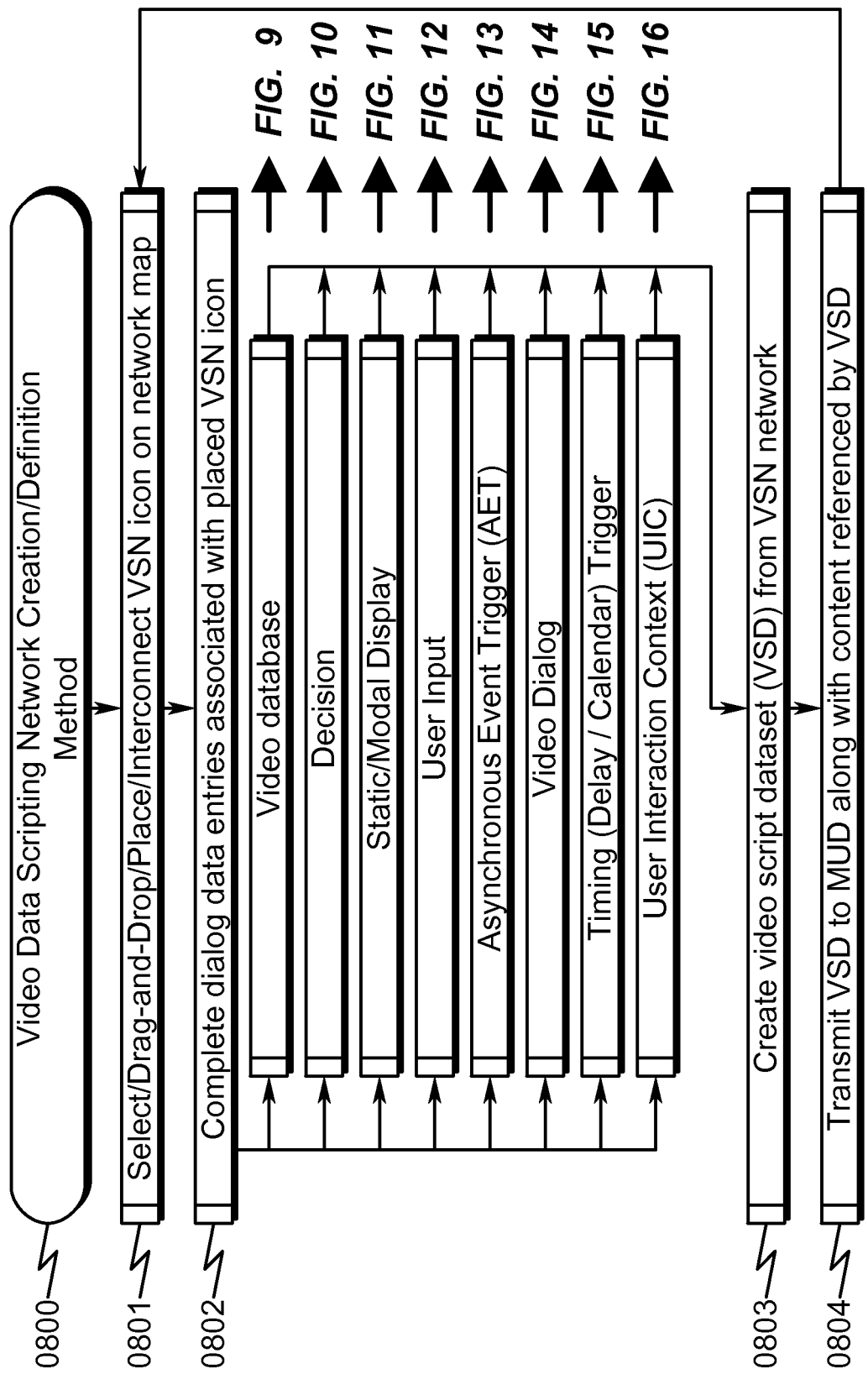
FIG. 8 illustrates a flowchart depicting an exemplary video data scripting network creation/definition method.
Figure 9:
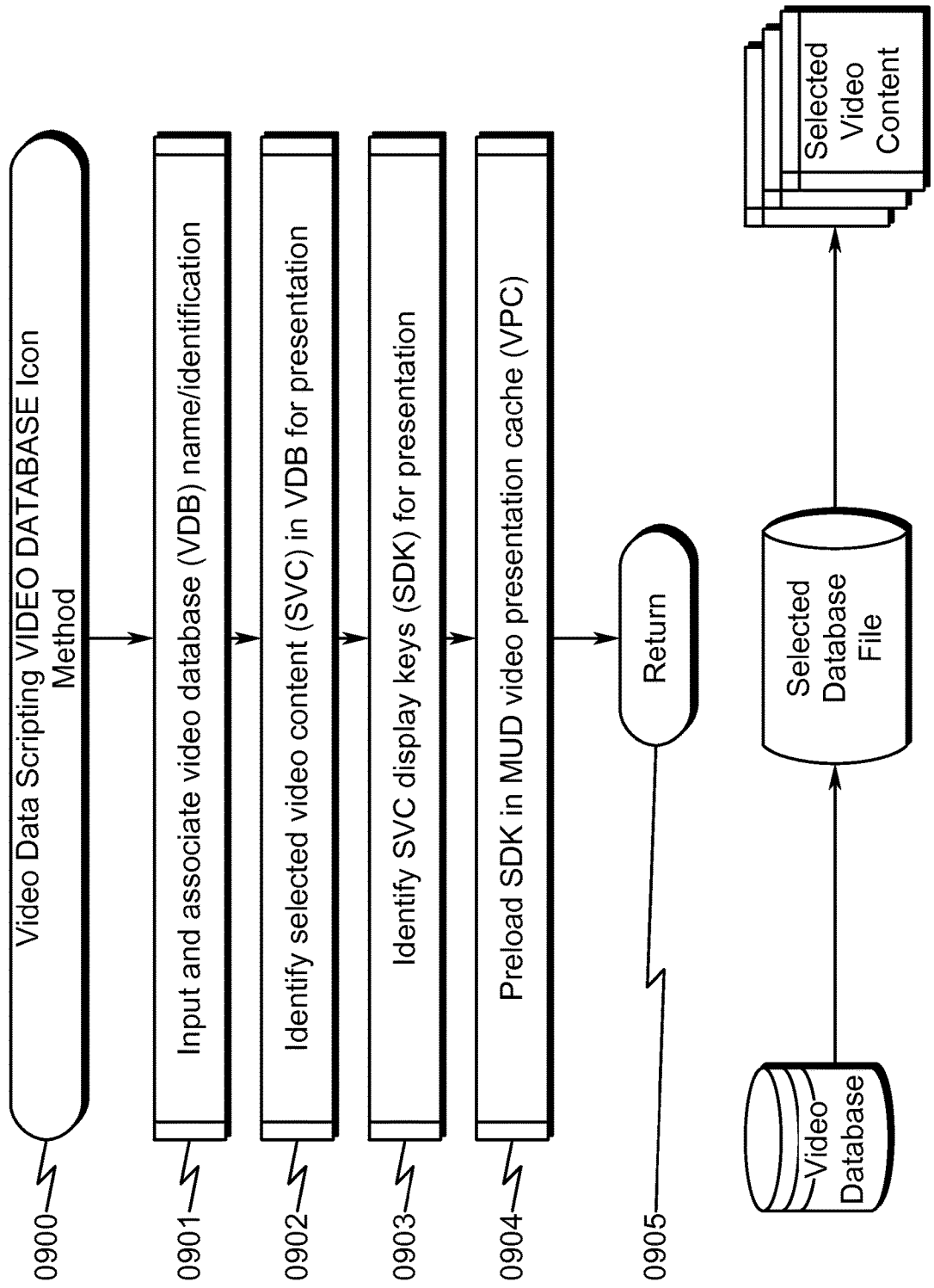
FIG. 9 illustrates a flowchart depicting an exemplary VSN VIDEO DATABASE icon definition method.

Associated with the exemplary VSN GUI system overview described above in FIG. 7 (0700) is a video data scripting network creation/definition method as depicted in FIG. 8 (0800) that comprises the following steps:

(1) Select, Drag-and-Dropping, Placing, and Interconnect a VSN video scripting icon (VSI) on/within a network map (0801);

(2) Completing dialog data entries associated with the placed VSN icon (0802) (exemplary methods to accomplish this are depicted in FIG. 9 (0900)—FIG. 16 (1600) and described below);

(3) Creating a video script dataset (VSD) from the visual VSN connected network (0803);

(4) Transmitting the VSD to the MUD along with content referenced by the VSD and proceeding to step (1) (0804).

One skilled in the art will recognize that these method steps may be augmented or rearranged without limiting the teachings of the present invention. This general method summary may be augmented by the various elements described herein to produce a wide variety of invention embodiments consistent with this overall design description.

Note that the implementation of the VSN permits complex video scripting scenarios to be constructed that may incorporate both synchronous as well as asynchronous operations and displays.

VSI Definition Example

VIDEO DATABASE (0900)

As depicted in FIG. 9 (0900), one presently preferred video scripting icon (VSI) comprises a VIDEO DATABASE icon that may be defined after placement using the following method:

(1) Input and associate video database (VDB) name/identification to identify the video source (0901);

(2) Identify selected video content (SVC) file in VDB for presentation (0902);

(3) Identify SVC display keys (SDK) for presentation to specify the portions of the SVC that are to be presented (0903); and (4) Preload SDK in MUD video presentation cache (VPC) (0904).

One skilled in the art will recognize that this icon definition process may be modified or augmented according to the application context of the present invention without limiting the invention scope.

VSI Definition Example

DECISION (1000)

Figure 10:
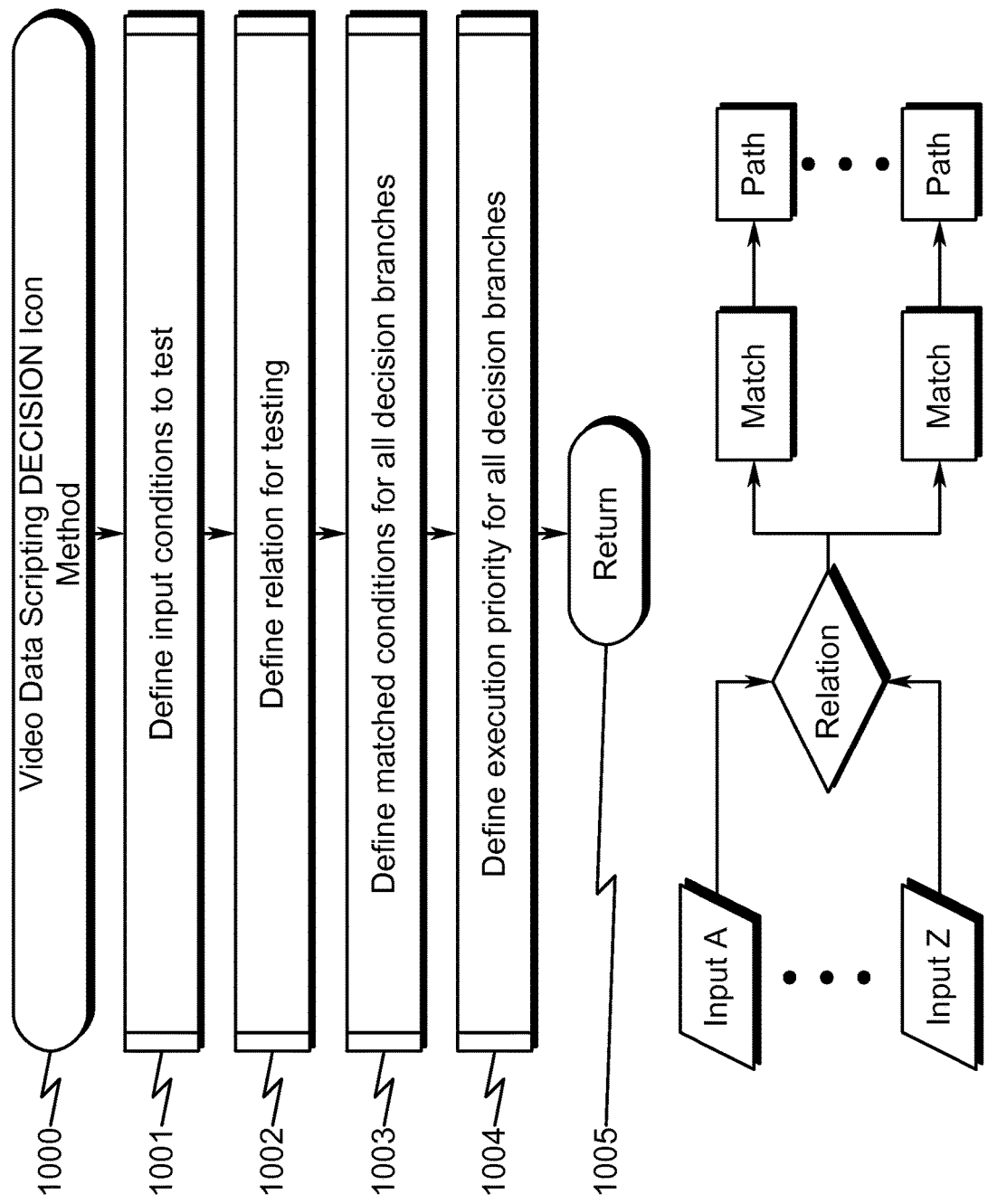
FIG. 10 illustrates a flowchart depicting an exemplary VSN DECISION icon definition method.

As depicted in FIG. 10 (1000), one presently preferred video scripting icon (VSI) comprises a DECISION icon that may be defined after placement using the following method:

(1) Define input conditions to test by the decision process (1001);

(2) Define the relation(s) for testing the decision (1002);

(3) Define matched conditions for all decision branches to allow for one or more paths to be activated based on satisfaction of the match conditions associated with the decision relations (1003); and (4) Defining a priority for each match condition to prioritize the execution of the decision exit paths (1004).

One skilled in the art will recognize that this icon definition process may be modified or augmented according to the application context of the present invention without limiting the invention scope.

VSI Definition Example

DISPLAY (1100)

Figure 11:
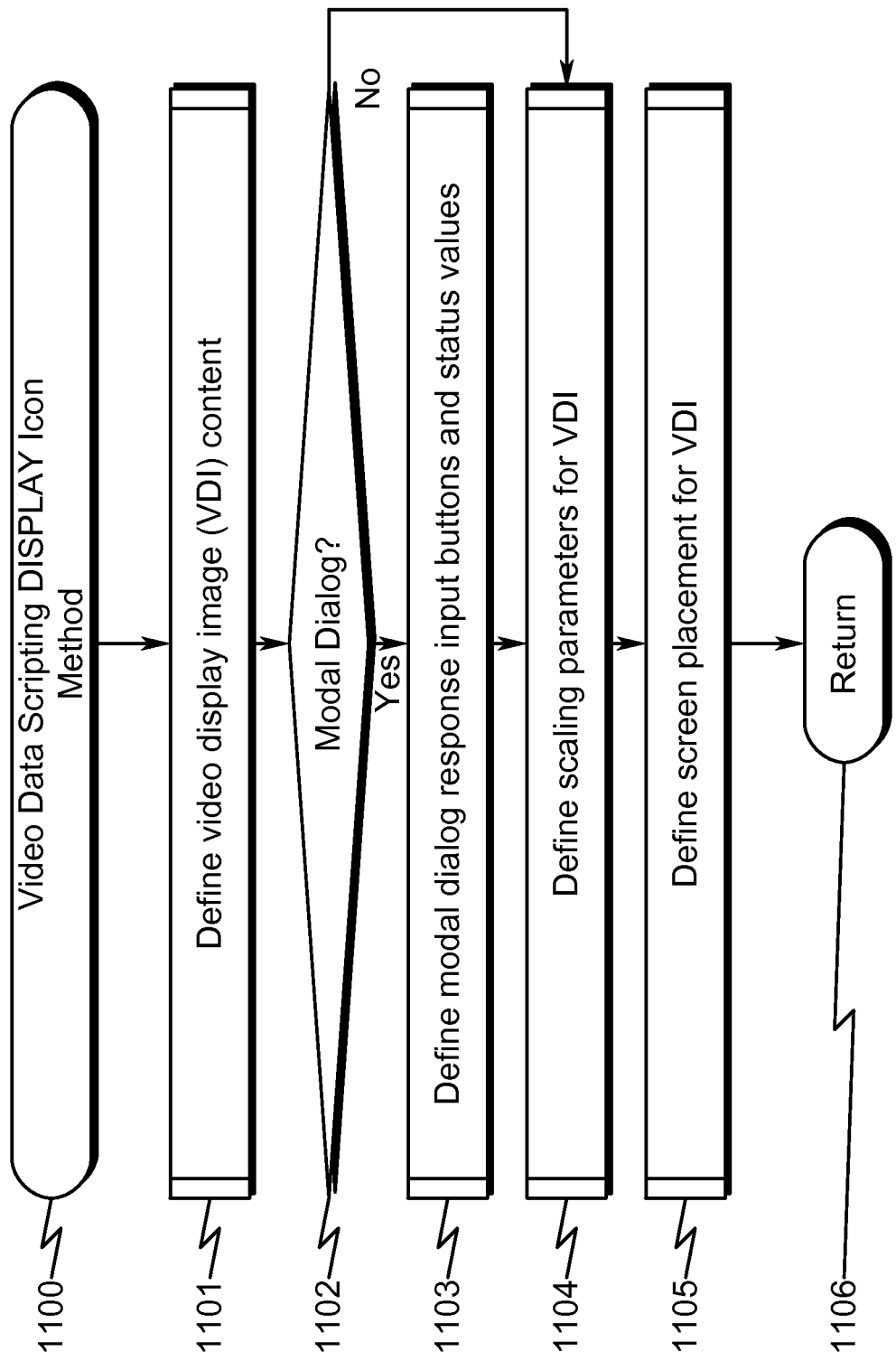
FIG. 11 illustrates a flowchart depicting an exemplary VSN DISPLAY icon definition method.

As depicted in FIG. 11 (1100), one presently preferred video scripting icon (VSI) comprises a DISPLAY icon that may be defined after placement using the following method:

(1) Define video display image (VDI) content by virtue of an editor or a reference to a VDI database (1101);

(2) Determining if the display is a modal dialog and if not, proceeding to step (4) (1102);

(3) Define modal dialog response input buttons and status values that are emitted from the display (1103);

(4) Define screen scaling parameters for the VDI (1104); and (5) Define screen placement for the VDI (1105).

One skilled in the art will recognize that this icon definition process may be modified or augmented according to the application context of the present invention without limiting the invention scope.

VSI Definition Example

USER INPUT (1200)

Figure 12:
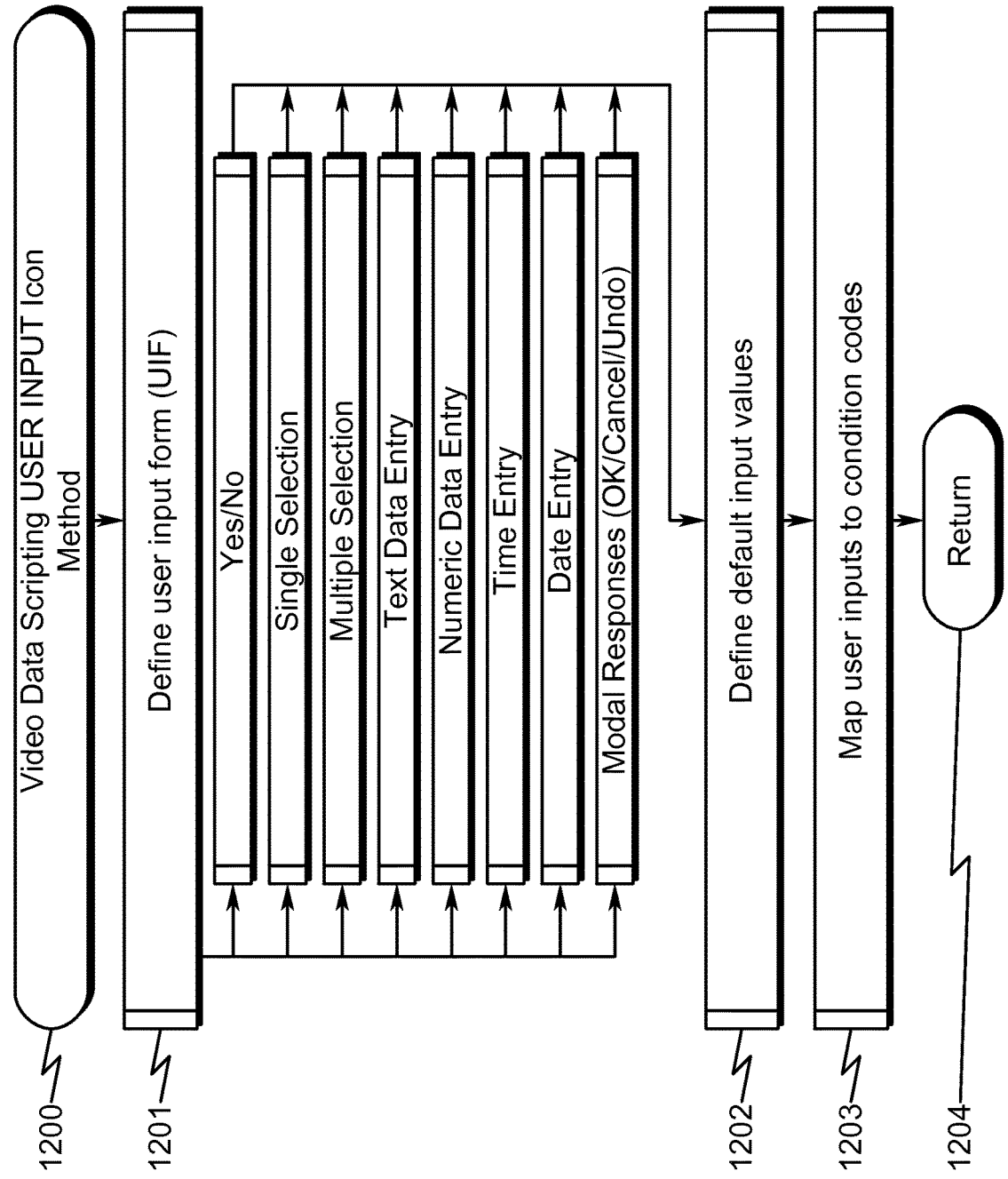
FIG. 12 illustrates a flowchart depicting an exemplary VSN USER INPUT icon definition method.

As depicted in FIG. 12 (1200), one presently preferred video scripting icon (VSI) comprises a USER INPUT icon that may be defined after placement using the following method:
(1) Define the user input form (UIF) to be accepted from the user which may include a variety of user input data types including but not limited to: yes/no, single selection, multiple selection, text data entry, numeric data entry, time entry, date entry, and modal responses (1201);
(2) Define default input values (1202); and
(3) Mapping user inputs to condition codes that are emitted by the VSI and which may be tested by a decision operator later in the VSN (1203).

One skilled in the art will recognize that this icon definition process may be modified or augmented according to the application context of the present invention without limiting the invention scope.

It should be noted that this VSI definition example may encompass situations in which a dialog is displayed to the user and input is entered by the user. Also, the source for user input and dialog display may be redirected from the MUD to another user input source such as an operator interface computer (OIC). In this scenario, a video script may be displayed among several output devices and input may be taken from a number of different input devices. The target destination for this user input may be directed to a host computer system or another data sink as indicated in the video scripting network (VSN).

VSI Definition Example

AET (1300)

Figure 13:
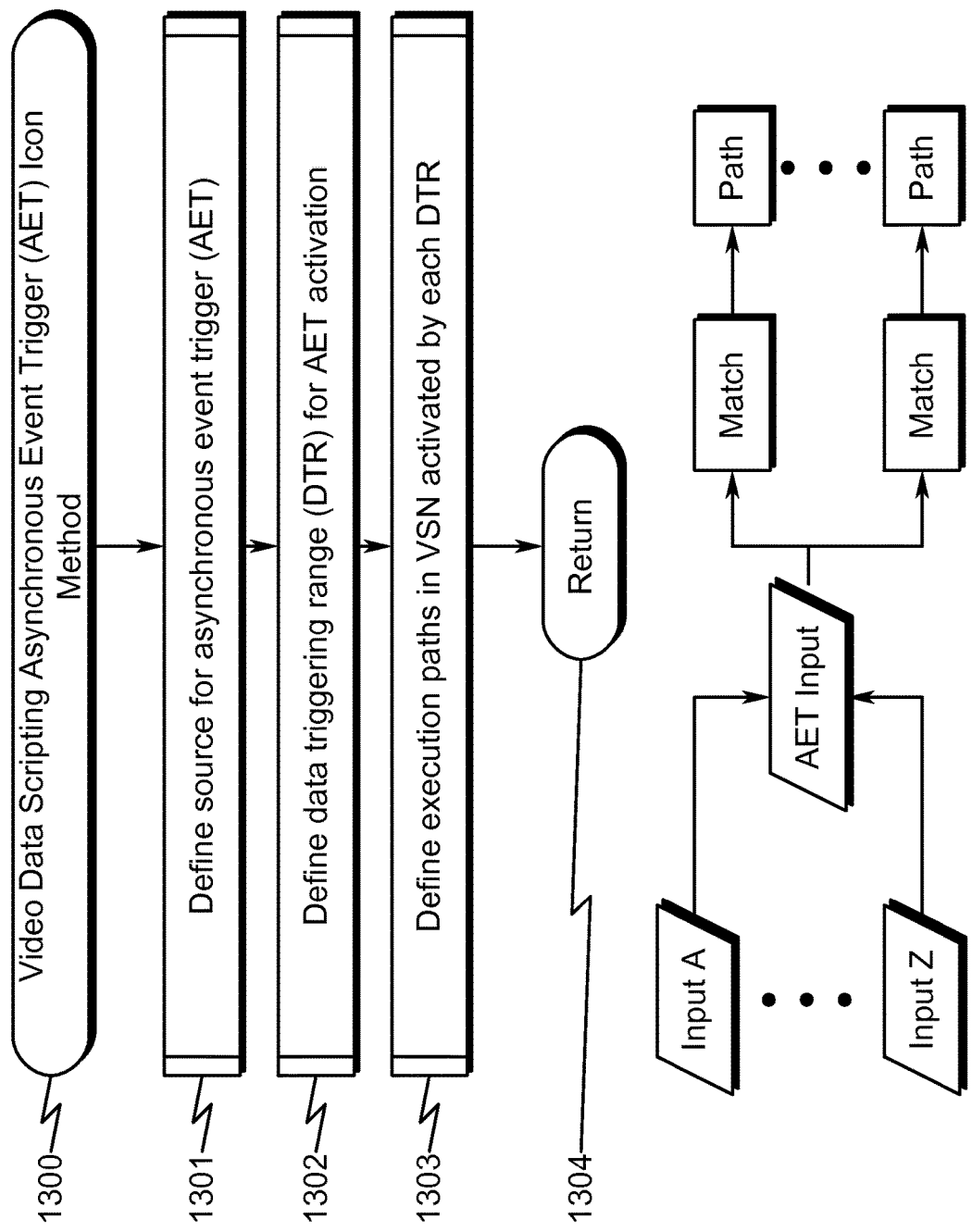
FIG. 13 illustrates a flowchart depicting an exemplary VSN ASYNCHRONOUS EVENT TRIGGER (AET) icon definition method.

As depicted in FIG. 13 (1300), one presently preferred video scripting icon (VSI) comprises an asynchronous event trigger (AET) icon that may be defined after placement using the following method:
(1) Define the icon or data source for the asynchronous event trigger (AET) (1301);
(2) Define data triggering range (DTR) for AET activation which may include the presence of data or a selected range or alert level associated with the collected data (1302); and
(3) Define execution paths in VSN activated by each DTR (this permits multiple paths to be activated based on each DTR) (1303).

One skilled in the art will recognize that this icon definition process may be modified or augmented according to the application context of the present invention without limiting the invention scope.

VSI Definition Example

VIDEO DIALOG (1400)

Figure 14:
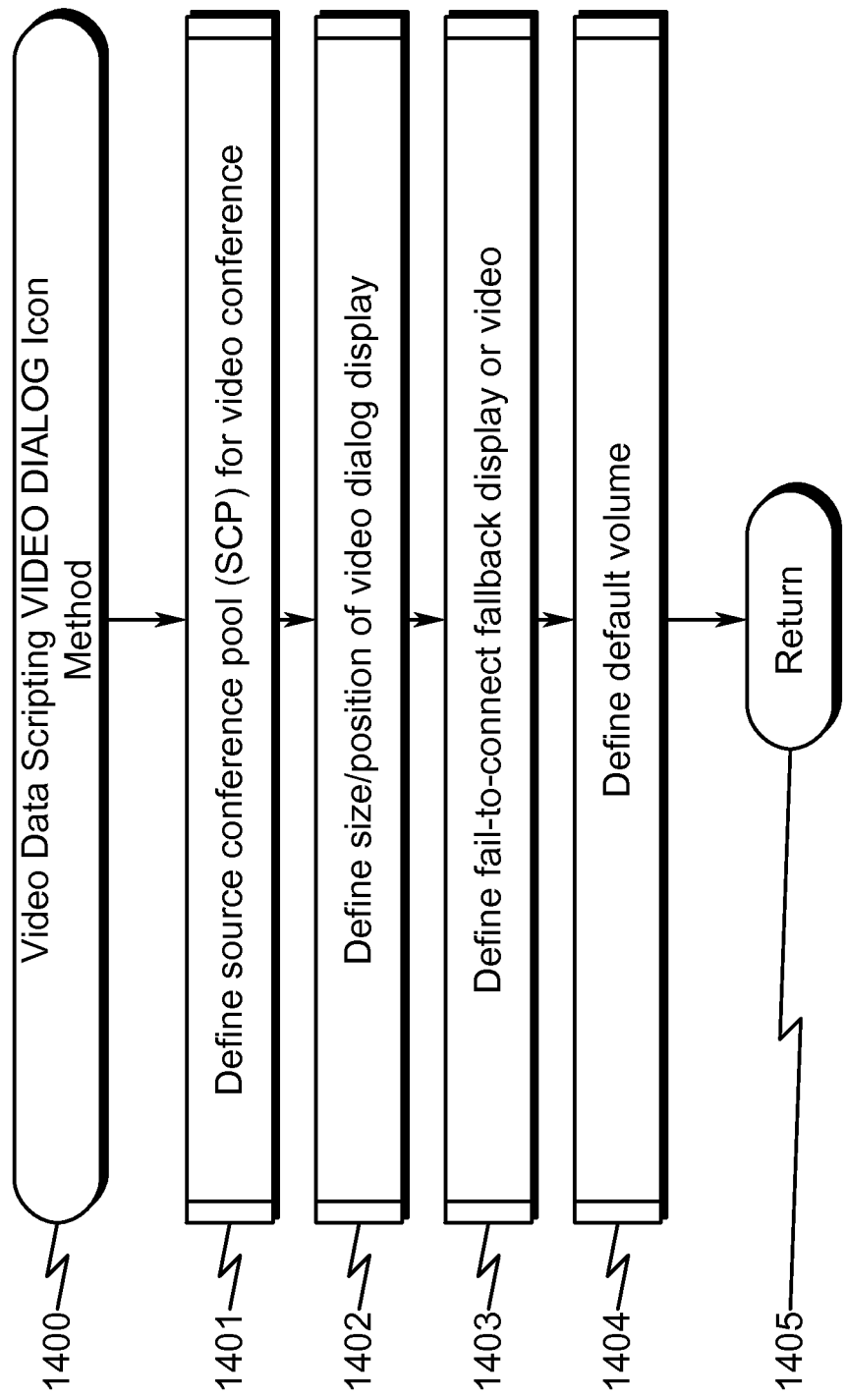
FIG. 14 illustrates a flowchart depicting an exemplary VSN VIDEO DIALOG icon definition method.

As depicted in FIG. 14 (1400), one presently preferred video scripting icon (VSI) comprises a VIDEO DIALOG icon that may be defined after placement using the following method:
(1) Define source conference pool (SCP) for video conference (this defines the connection to a remote pool of individuals associated with the video conference) (1401);
(2) Define size/position of video dialog display on the user display device (1402);
(3) Define fail-to-connect fallback display or video to be displayed if a video conference cannot be established (1403); and
(4) Define default volume for multimedia audio (1404).

One skilled in the art will recognize that this icon definition process may be modified or augmented according to the application context of the present invention without limiting the invention scope.

VSI Definition Example

TIMING (1500)

Figure 15:
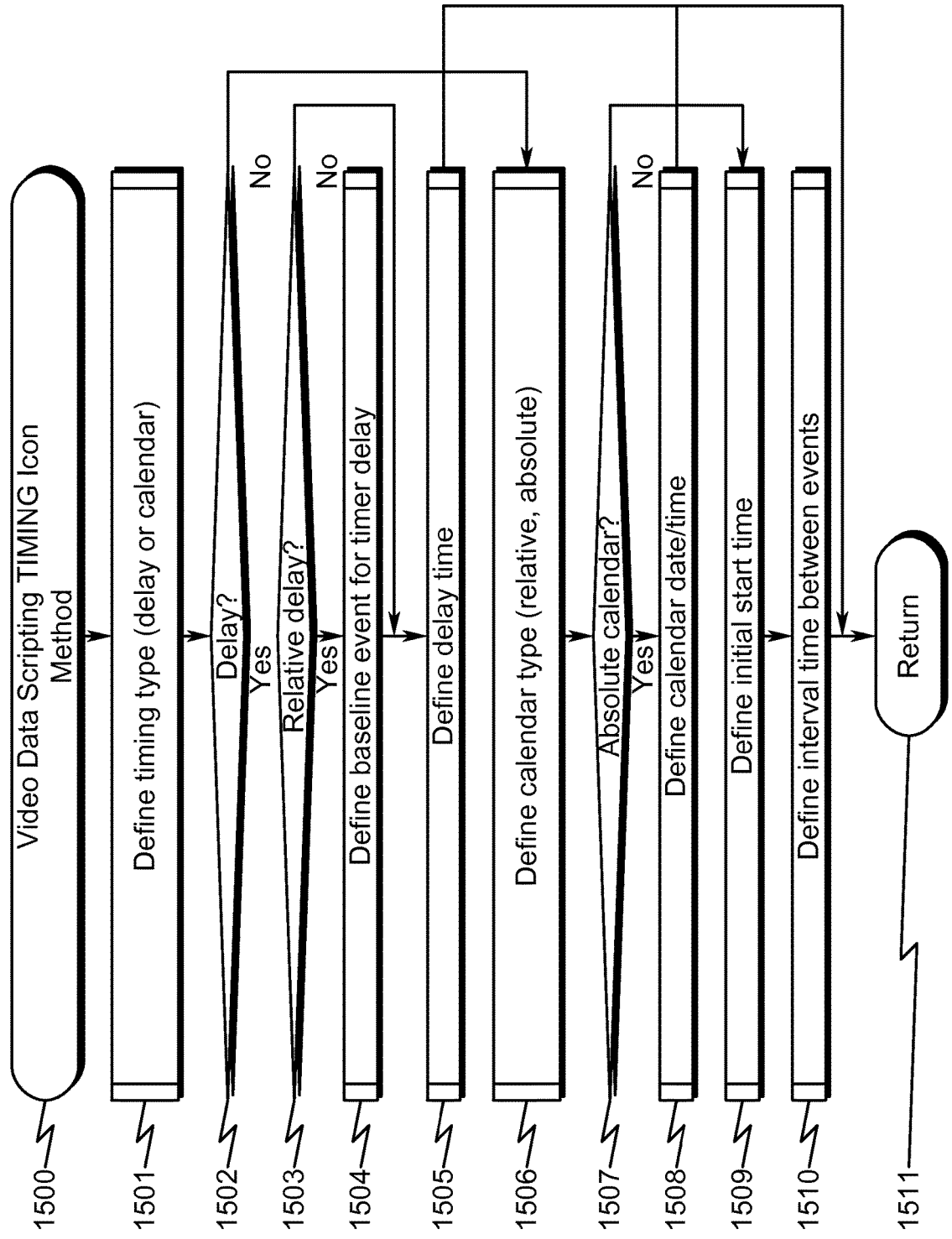
FIG. 15 illustrates a flowchart depicting an exemplary VSN TIMING icon definition method.

As depicted in FIG. 15 (1500), one presently preferred video scripting icon (VSI) comprises a TIMING icon that may be defined after placement using the following method:
(1) Define timing icon type (delay or calendar) (1501);
(2) Determine if the icon type is a delay icon, and if not, proceeding to step (6) (1502);
(3) Determine if the delay type is a relative delay, and if not, proceeding to step (5) (1503);
(4) Define baseline event for timer delay (1504);
(5) Define the delay time and proceed to step (11) (1505);
(6) Define calendar type (relative or absolute) (1506);
(7) Determine if the calendar type is absolute, and if not, proceeding to step (9) (1507);
(8) Define the absolute calendar date/time and proceed to step (11) (1508);
(9) Define the initial start time (1509);
(10) Define interval time between event triggers (1510);
(11) Terminating the TIMING icon definition process (1511).

One skilled in the art will recognize that this icon definition process may be modified or augmented according to the application context of the present invention without limiting the invention scope.

VSI Definition Example

UIC (1600)

Figure 16:
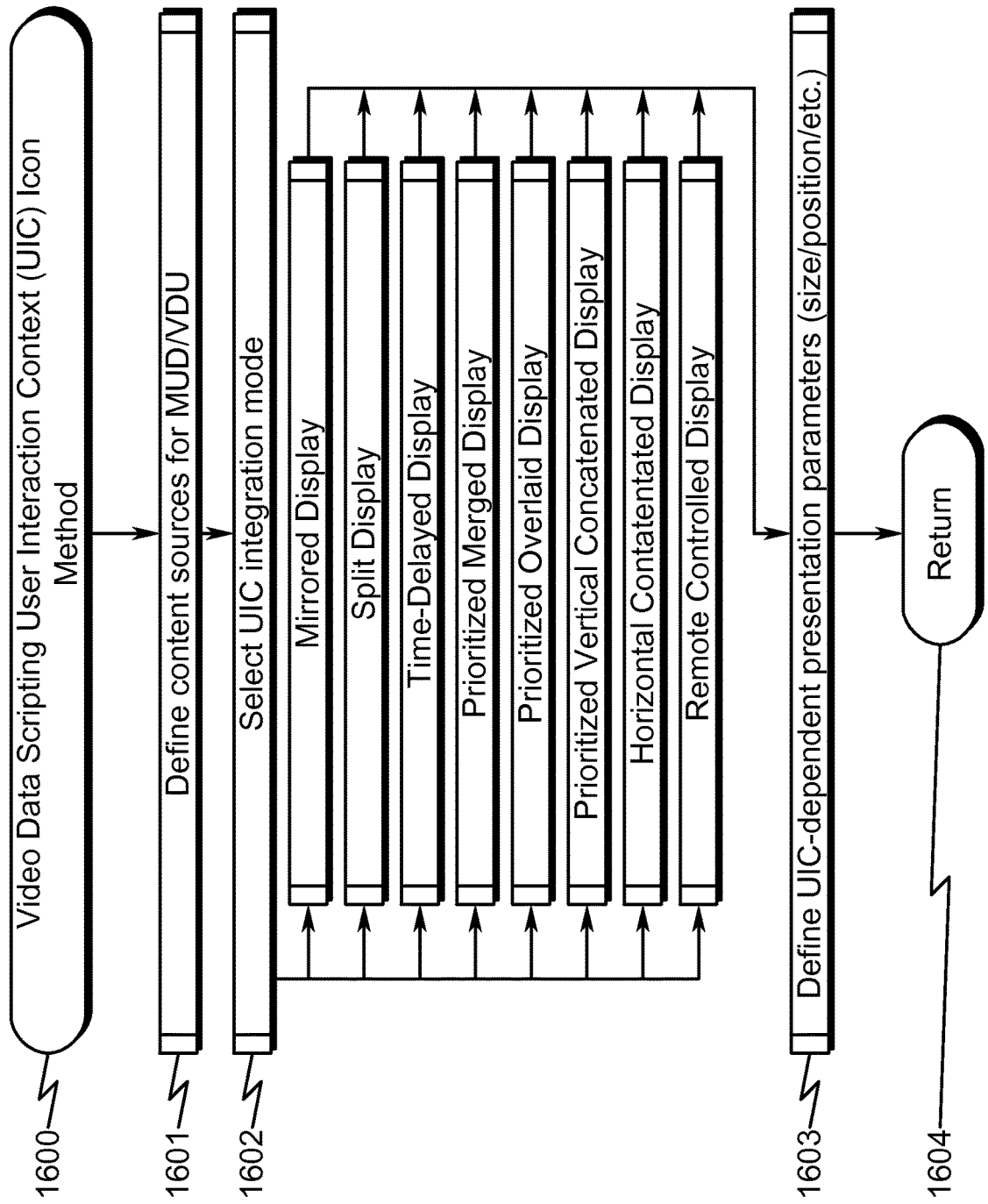
FIG. 16 illustrates a flowchart depicting an exemplary VSN USER INTERACTION CONTEXT (UIC) icon definition method.

As depicted in FIG. 16 (1600), one presently preferred video scripting icon (VSI) comprises a user interaction context (UIC) icon that may be defined after placement using the following method:
(1) Define content sources for MUD/VDU display (1601);
(2) Select UIC integration mode (examples of these modes are described further in the VIDEO DATA EXTENSION SYSTEM AND METHOD patent application included herein by reference and may include exemplary UIC modes such as: mirrored display, split display, time-delayed display, prioritized merged display, prioritized overlaid display, prioritized vertical concatenated display, horizontal concatenated display, remote controlled display, etc.) (1602); and
(3) Define UIC-dependent presentation parameters (size/position/etc.) (1603).

One skilled in the art will recognize that this icon definition process may be modified or augmented according to the application context of the present invention without limiting the invention scope.

PHP Control of Scripts

The present invention anticipates that any VSN executed on the VCU may be triggered for activation by scripts driven by a patient healthcare plan (PHP) as defined by the HEALTHCARE DELIVERY SYSTEM AND METHOD patent application incorporated herein by reference. Thus, the MUD as described herein may communicate with the HSC to download PHP scripts that interoperate with medical instrumentation devices (MIDs) to collect patient medical data as well as prompt the user with queries and accept responses to collectively trigger alerts and data messages to remote healthcare personnel serviced by a healthcare web server (HWS) (which may comprise the HCS as described herein). Within this overall context of healthcare management, the PHP may also incorporate VSN data structures (VSD) that coordinate the presentation of user input and output functions among the MUD and VDU to provide an integrated user input/output data collection and display experience.

Embedded Synchronization Data

The VSN and corresponding VSD may incorporate internal synchronization data to allow certain points in the video script to trigger external processes and/or events. This may be useful (for example) in situations where a caregiver is requested to perform an evaluation of the patient in response to a video script presented to the patient, and perform this evaluation at a set point in the display process. This triggering of synchronized processes and/or events may occur in parallel or with patient video presentations or in a synchronous manner in which patient video is stalled/delayed during the caregiver interaction. This capability permits internal video threads within the VSD to perform additional operations associated with the patient and displayed video without the requirement that a highly experienced computer programmer construct the overall interaction with the patient. Thus, the overall nature of the GUI-based video scripting system as disclosed herein aids the deployment of multi-threaded video without the need for highly experienced computer programmers to implement the patient interaction context.

Multiple Video Threads

The video scripting system as described herein is anticipated in some preferred embodiments to incorporate the capability for separate video display threads that are synchronized with one another but not necessarily displayed on the same visual display. For example, it is anticipated that in some circumstances a video display may be presented to a patient and have an associated caregiver video display associated with the patient presentation. This capability in conjunction with embedded synchronization data can permit (for example) the gathering of data by a caregiver in response to a synchronized video thread that is presented to a patient. An example of this might be the gathering of caregiver scores based on an observation of the patient in response to virtual rehabilitation video scripts that are presented to the patient. In this circumstance the patient response can be scored by the caregiver at set synchronization points and these responses logged to the patient history database (PHD).

Preferred Embodiment System Summary

The present invention preferred exemplary system embodiment anticipates a wide variety of variations in the basic theme of construction, but can be generalized as a dynamic video scripting system comprising:
(a) host computer system (HSC);
(b) mobile user device (MUD); and
(c) computer communication network (CCN);
wherein
said HCS is configured with a graphical user interface (GUI) operable to accept commands by said HCS to define a video script network (VSN) on said GUI;
said VSN comprises an interconnected network of GUI scripting icons (GSIs) selected from a group consisting of: audio/video content (AVC), decision-based content (DBC), user query/response (UQR), and asynchronous event trigger (AET);
said HCS is configured to translate said VSN into a video script dataset (VSD) describing the interconnection and function of said GSIs;
said HCS is configured to transmit said VSD to said MUD over said CCN;
said MUD is configured to interpret said VSD in the context of a mobile scripting engine (MSE) operating under control of said MUD;
said MSE is configured to execute said VSD to control the display and input functions of said MUD; and
said MSE is configured to implement a user interface context (UIC) on said MUD that dynamically presents a display on said MUD and accepts input from said MUD based on execution of said VSD by said MSE.

This general system summary may be augmented by the various elements described herein to produce a wide variety of invention embodiments consistent with this overall design description.

Preferred Embodiment Method Summary

The present invention preferred exemplary method embodiment anticipates a wide variety of variations in the basic theme of implementation, but can be generalized as a dynamic video scripting method, the method operating in conjunction with a dynamic video scripting system comprising:
(a) host computer system (HSC);
(b) mobile user device (MUD); and
(c) computer communication network (CCN);
wherein
said HCS is configured with a graphical user interface (GUI) operable to accept commands by said HCS to define a video script network (VSN) on said GUI;
said VSN comprises an interconnected network of GUI scripting icons (GSIs) selected from a group consisting of: audio/video content (AVC), decision-based content (DBC), user query/response (UQR), and asynchronous event trigger (AET);
said HCS is configured to translate said VSN into a video script dataset (VSD) describing the interconnection and function of said GSIs;
said HCS is configured to transmit said VSD to said MUD over said CCN;
said MUD is configured to interpret said VSD in the context of a mobile scripting engine (MSE) operating under control of said MUD;
said MSE is configured to execute said VSD to control the display and input functions of said MUD; and
said MSE is configured to implement a user interface context (UIC) on said MUD that dynamically presents a display on said MUD and accepts input from said MUD based on execution of said VSD by said MSE;

wherein the method comprises the steps of:
(1) with the HCS, accepting input from a user to define the VSN using the GUI;
(2) with the HCS, translating the VSN into the VSD;
(3) with the HCS, transmitting the VSD to the MUD over the CCN;
(4) with the MUD, executing the VSD to control the display and input functions of the MUD; and
(5) with the MUD, dynamically implementing the UIC to coordinate user interaction with the MUD under control of the VSD.

One skilled in the art will recognize that these method steps may be augmented or rearranged without limiting the teachings of the present invention. This general method summary may be augmented by the various elements described herein to produce a wide variety of invention embodiments consistent with this overall design description.

System/Method Variations

The present invention anticipates a wide variety of variations in the basic theme of construction. The examples presented previously do not represent the entire scope of possible usages. They are meant to cite a few of the almost limitless possibilities.

This basic system and method may be augmented with a variety of ancillary embodiments, including but not limited to:

An embodiment wherein the CCN comprises the Internet.
An embodiment wherein the MSE is configured to execute the VSD in a synchronous manner to present the AVC referenced within the VSD on the MUD.
An embodiment wherein the MSE is configured to execute the VSD in a synchronous manner to present the DBC referenced within the VSD on the MUD.
An embodiment wherein the MSE is configured to execute the VSD in a synchronous manner to present output from the UQR referenced within the VSD on the MUD.
An embodiment wherein the MSE is configured to execute the VSD in a synchronous manner to accept input from the UQR referenced within the VSD from the MUD.
An embodiment wherein the MSE is configured to execute the VSD in an asynchronous manner to accept the AETs referenced within the VSD from remote data content (RDC) available to the MUD.
An embodiment wherein the UQR is selected from a group consisting of: single selections; multiple selections; and yes/no responses.
An embodiment wherein the AETs are defined by data selected from a group consisting of: input data entered as a result of the UQR; elapsed timer values; calendar time values; periodic timer values; and remote event triggers (RETS) activated by the HSC.
An embodiment wherein the AETs are defined by data derived from a medical instrumentation device (MID) selected from a group consisting of: weight scale; pulse oximeter; blood pressure meter; and blood glucose meter.
An embodiment wherein the UIC is triggered for activation by a patient healthcare plan (PHP) executing within the context of the MUD.

One skilled in the art will recognize that other embodiments are possible based on combinations of elements taught within the above invention description.

Generalized Computer Usable Medium

In various alternate embodiments, the present invention may be implemented as a computer program product for use with a computerized computing system. Those skilled in the art will readily appreciate that programs defining the functions defined by the present invention can be written in any appropriate programming language and delivered to a computer in many forms, including but not limited to: (a) information permanently stored on non-writeable storage media (e.g., read-only memory devices such as ROMs or CD-ROM disks); (b) information alterably stored on writeable storage media (e.g., floppy disks and hard drives); and/or (c) information conveyed to a computer through communication media, such as a local area network, a telephone network, or a public network such as the Internet. When carrying computer readable instructions that implement the present invention methods, such computer readable media represent alternate embodiments of the present invention.

As generally illustrated herein, the present invention system embodiments can incorporate a variety of computer readable media that comprise computer usable medium having computer readable code means embodied therein. One skilled in the art will recognize that the software associated with the various processes described herein can be embodied in a wide variety of computer accessible media from which the software is loaded and activated. Pursuant to In re Beauregard, 35 USPQ2d 1383 (U.S. Pat. No. 5,710,578), the present invention anticipates and includes this type of computer readable media within the scope of the invention. Pursuant to In re Nuijten, 500 F.3d 1346 (Fed. Cir. 2007) (U.S. patent application Ser. No. 09/211,928), the present invention scope is limited to computer readable media wherein the media is both tangible and non-transitory.

CONCLUSION

A system and method dynamically presenting video content based on a visually-defined scripting editor that defines a user presentation context (UPC) based on audio/video content, user query/responses, and one or more asynchronous event triggers (AETs) has been disclosed. The system incorporates a graphical user interface (GUI) based scripting editor operating on a host computer system (HCS) that enables visual definition of an interconnected video script network (VSN) that may include synchronously displayed content, decision-based content, and/or content dictated by the AETs. The VSN is converted to a video script dataset (VSD) by the HCS and then transmitted over a computer communication network (CCN) to a mobile user device (MUD) that executes the VSD in a user interface context (UIC) that may include the MUD, other devices such as a video display unit (VDU), and/or external data sourcing devices that may constitute the sources for the AETs.

What is claimed is:
1. A dynamic video scripting system comprising:
(a) host computer system (HSC);
(b) mobile user device (MUD);
(c) computer communication network (CCN); and
(d) operator interface computer (OIC);
wherein
said HCS is configured with a graphical user interface (GUI) operable to accept commands by said HCS to define a video script network (VSN) on said GUI;
said VSN comprises an interconnected network of GUI scripting icons (GSIs) selected from a group consisting of: audio/video content (AVC), decision-based content (DBC), use query/response (UQR), and asynchronous event trigger (AET);

said HCS is configured to translate said VSN into a video script dataset (VSD) describing the interconnection and function of said GSIs, wherein the VSD references data retrieved from a media database (MDB) and the VSN describes sequencing of multimedia content retrieved from the MDB and interaction of the multimedia content with a user, wherein the VSN further permits internal video threads within the VSD to perform additional operations associated with the user and displayed video without interaction from the user;

said HCS is configured to transmit said VSD to said MUD over said CCN;

said MUD is configured to execute a mobile scripting engine (MSE) operating under control of said MUD, wherein the MSE interprets the VSD and retrieves the multimedia content from the MDB for presentation to the user on the MUD;

said MSE is configured to execute said VSD to control the display and input functions of said MUD;

said MSE is configured to implement a user interface context (UIC) on said MUD that dynamically presents a display on said MUD and accepts input from said MUD based on execution of said VSD by said MSE, wherein the UIC defines integration of the multimedia content on the MUD; and said UIC is triggered for activation by a patient healthcare plan (PHP) executing within the context of said MUD, wherein the PHP is configurable from the OIC and comprises additional GSIs for translation and incorporation into the VSD, wherein the additional GSIs coordinate presentation of user input and output functions of the MUD to provide an integrated user input output data collection and display.

2. The dynamic video scripting system of claim 1 wherein said MSE is configured to execute said VSD in a synchronous manner to present said AVC referenced within said VSD on said MUD.

3. The dynamic video scripting system of claim 1 wherein said MSE is configured to execute said VSD in a synchronous manner to present said DBC referenced within said VSD on said MUD.

4. The dynamic video scripting system of claim 1 wherein said MSE is configured to execute said VSD in a synchronous manner to present output from said UQR referenced within said VSD on said MUD.

5. The dynamic video scripting system of claim 1 wherein said MSE is configured to execute said VSD in a synchronous manner to accept input from said UQR referenced within said VSD from said MUD.

6. The dynamic video scripting system of claim 1 wherein said MSE is configured to execute said VSD in an asynchronous manner to accept said AETs referenced within said VSD from remote data content (RDC) available to said MUD.

7. The dynamic video scripting system of claim 1 wherein said UQR is selected from a group consisting of: single selections; multiple selections; and yes/no responses.

8. The dynamic video scripting system of claim 1 wherein said AETs are defined by data selected from a group consisting of: input data entered as a result of said UQR; elapsed timer values; calendar time values; periodic timer values; and remote event triggers (RETS) activated by said HCS.

9. The dynamic video scripting system of claim 1 wherein said AETs are defined by data derived from a medical instrumentation device (MID) selected from a group consisting of: weight scale; pulse oximeter; blood pressure meter; and blood glucose meter.

10. A dynamic video scripting method, said method operating in conjunction with a dynamic video scripting system comprising:
    (a) host computer system (HSC);
    (b) mobile user device (MUD);
    (c) computer communication network (CCN); and
    (d) operator interface computer (OIC);
    wherein said HCS is configured with a graphical user interface (GUI) operable to accept commands by said HCS to define a video script network (VSN) on said GUI;

said VSN comprises an interconnected network of GUI scripting icons (GSIs) selected from a group consisting of: audio/video content (AVC), decision-based content (DBC), user query/response (UQR), and asynchronous event trigger (AFT);

said HCS is configured to translate said VSN into a video script dataset (VSD) describing the interconnection and function of said GSIs, wherein the VSD references data retrieved from a media database (MDB) and the VSN describes sequencing of multimedia content retrieved from the MDB and interaction of the multimedia content with a user, wherein the VSN further permits internal video threads within the VSD to perform additional operations associated with the user and displayed video without interaction from the user;

said HCS is configured to transmit said VSD to said MUD over said CCN;

said MUD is configured execute a mobile scripting engine (MSE) operating under control of said MUD, wherein the MSE interprets the VSD and retrieves the multimedia content from the MDB for presentation to the user on the MUD;

said MSE is configured to execute said VSD to control the display and input functions of said MUD;

said MSE is configured to implement a user interface context (UIC) on said MUD that dynamically presents a display on said MUD and accepts input from said MUD based on execution of said VSD by said MSE, wherein the UIC defines integration of the multimedia content on the MUD; and said UIC is triggered for activation by a patient healthcare plan (PHP) executing within the context of said MUD, wherein the PHP is configurable from the OIC and comprises additional GSIs for translation and incorporation into the VSD, wherein the additional GSIs coordinate presentation of user input and output functions of the MUD to provide an integrated user input/output data collection and display;

wherein said method comprises the steps of:
    (1) with said HCS, accepting input from a user to define said VSN using said GUI;
    (2) with said HCS, translating said VSN into said VSD;
    (3) with said HCS, transmitting said VSD to said MUD;
    (4) with said MUD, executing said VSD to control the display and input functions of said MUD; and
    (5) with said MUD, dynamically implementing said UIQ to coordinate user interaction with said MUD under control of said VSD.

11. The dynamic video scripting method of claim 10 wherein said MSE is configured to execute said VSD in a synchronous manner to present said AVC referenced within said VSD on said MUD.

12. The dynamic video scripting method of claim 10 wherein said MSE is configured to execute said VSD in a synchronous manner to present said DBC referenced within said VSD on said MUD.

13. The dynamic video scripting method of claim 10 wherein said MSE is configured to execute said VSD in a synchronous manner to present output from said UQR referenced within said VSD on said MUD.

14. The dynamic video scripting method of claim 10 wherein said MSE is configured to execute said VSD in a synchronous manner to accept input from said UQR referenced within said VSD from said MUD.

15. The dynamic video scripting method of claim 10 wherein said MSE is configured to execute said VSD in an asynchronous manner to accept said AETs referenced within said VSD from remote data content (RDC) available to said MUD.

16. The dynamic video scripting method of claim 10 wherein said UQR is selected from a group consisting of: single selections; multiple selections; and yes/no responses.

17. The dynamic video scripting method of claim 10 wherein said AETs are defined by data selected from a group consisting of input data entered as a result of said UQR; elapsed timer values; calendar time values; periodic timer values; and remote event triggers (RETs) activated by said HSC.

18. The dynamic video scripting method of claim 10 wherein said AETs are defined by data derived from a medical instrumentation device (MID) selected from a group consisting of: weight scale; pulse oximeter; blood pressure meter; and blood glucose meter.

19. A tangible non-transitory computer usable medium having computer-readable program code means embodied thereon comprising a dynamic video scripting method, said method operating in conjunction with a dynamic video scripting system comprising:
(a) host computer system (HSC);
(b) mobile user device (MUD);
(c) computer communication network (CCN); and
(d) operator interface computer (OIC);
wherein
said HCS is configured with a graphical user interface (GUI) operable to accept commands by said HCS to define a video script network (VSN) on said GUI;
said VSN comprises an interconnected network of GUI scripting icons (GSIs) selected from a group consisting of: audio/video content (AVC), decision-based content (DBC), user query/response (UQR), and asynchronous event trigger (AET);
said HCS is configured to translate said VSN into a video script dataset (VSD) describing the interconnection and function of said GSIs, wherein the VSD references data retrieved from a media database (MDB) and the VSN describes sequencing of multimedia content retrieved from the MDB and interaction of the multimedia content with a user, wherein the VSN further permits internal video threads within the VSD to perform additional operations associated with the user and displayed video without interaction from the user;
said HCS is configured to transmit said VSD to said MUD over said CCN;
said MUD is configured to execute a mobile scripting engine (MSE) operating under control of said MUD, wherein the MSE interprets said VSD and retrieves the multimedia content from the MDB for presentation to the user on the MUD;
said MSE is configured to execute said VSD to control the display and input functions of said MUD;
said MSE is configured to implement a user interface context (UIC) on said MUD that dynamically presents a display on said MUD and accepts input from said MUD based on execution of said VSD by said MSE, wherein the UIC defines integration of the multimedia content on the MUD; and
said UIC is triggered for activation by a patient healthcare plan (PHP) executing within the context of said MUD, wherein the PHP is configurable from the OIC and comprises additional GSIs for translation and incorporation into the VSD, wherein the additional GSIs coordinate presentation of user input and output functions of the MUD to provide an integrated user input/output data collection and display;
wherein said method comprises the steps of:
(1) with said HCS, accepting input from a user to define said VSN using said GUI;
(2) with said HCS, translating said VSN into said VSD;
(3) with said HCS, transmitting said VSD to said MUD;
(4) with said MUD, executing said VSD to control the display and input functions of said MUD; and
(5) with said MUD, dynamically implementing said UIC to coordinate user interaction with said MUD under control of said VSD.

20. The computer usable medium of claim 19 wherein said MSE is configured to execute said VSD in a synchronous manner to present said AVC referenced within said VSD on said MUD.

21. The computer usable medium of claim 19 wherein said MSE is configured to execute said VSD in a synchronous manner to present said DBC referenced within said VSD on said MUD.

22. The computer usable medium of claim 19 wherein said MSE is configured to execute said VSD in a synchronous manner to present output from said UQR referenced within said VSD on said MUD.

23. The computer usable medium of claim 19 wherein said MSE is configured to execute said VSD in a synchronous manner to accept input from said UQR referenced within said VSD from said MUD.

24. The computer usable medium of claim 19 wherein said MSE is configured to execute said VSD in an asynchronous manner to accept said AETs referenced within said VSD from remote data content (RDC) available to said MUD.

25. The computer usable medium of claim 19 wherein said UQR is selected from a group consisting of: single selections; multiple selections; and yes/no responses.

26. The computer usable medium of claim 19 wherein said AETs are defined by data selected from a group consisting of: input data entered as a result of said UQR; elapsed timer values; calendar time values; periodic timer values; and remote event triggers (RETS) activated by said HSC.

27. The computer usable medium of claim 19 wherein said AETs are defined by data derived from a medical instrumentation device (MID) selected from a group consisting of: weight scale; pulse oximeter; blood pressure meter; and blood glucose meter.

* * * * *